US012797191B2

(12) United States Patent
Bowe et al.

(10) Patent No.: US 12,797,191 B2
(45) Date of Patent: Nov. 17, 2026

(54) CRIMPER WITH CHANNELS FOR APPLYING FLUID TO LEAFLETS OF A VALVE PROSTHESIS DURING CRIMPING

(71) Applicant: MEDTRONIC, INC., Minneapolis, MN (US)

(72) Inventors: Jason Bowe, Blaine, MN (US); Matthew Ziebol, Blaine, MN (US); Alkindi Kibria, Irvine, CA (US); Victoria Ung, Santa Rosa, CA (US); Matthew Genovese, Windsor, CA (US); Yogesh Darekar, Irvine, CA (US); Matthew Baldwin, Santa Rosa, CA (US); Radhika Bhargav, Mountain View, CA (US); Brian Castelli, Santa Rosa, CA (US)

(73) Assignee: MEDTRONIC, INC., Minneapolis, MN (US)

(*) Notice: Subject to any disclaimer, the term of this patent is extended or adjusted under 35 U.S.C. 154(b) by 239 days.

(21) Appl. No.: 18/833,058

(22) PCT Filed: Jan. 31, 2023

(86) PCT No.: PCT/IB2023/050841
§ 371 (c)(1),
(2) Date: Jul. 25, 2024

(87) PCT Pub. No.: WO2023/148615
PCT Pub. Date: Aug. 10, 2023

(65) Prior Publication Data
US 2025/0107890 A1 Apr. 3, 2025

Related U.S. Application Data

(60) Provisional application No. 63/306,228, filed on Feb. 3, 2022.

(51) Int. Cl.
*A61F 2/24* (2006.01)
*B21D 39/04* (2006.01)

(52) U.S. Cl.
CPC .......... *A61F 2/2427* (2013.01); *B21D 39/046* (2013.01); *A61F 2240/001* (2013.01)

(58) Field of Classification Search
CPC .... A61F 2/2427; A61F 2/2418; A61F 2/9524; A61F 2/958; A61F 2240/001; B21D 39/046; B21D 11/08
(Continued)

(56) References Cited

U.S. PATENT DOCUMENTS 7,284,401 B2 * 10/2007 Larson .................... A61F 2/95 72/402
9,757,232 B2 9/2017 Peterson et al.
(Continued)

FOREIGN PATENT DOCUMENTS

WO 2021202173 A1 10/2021

OTHER PUBLICATIONS

International Search Report and Written Opinion issued May 4, 2023 in Intl. Appl. No. PCT/IB2023/050841.

*Primary Examiner* — Tuan V Nguyen
(74) *Attorney, Agent, or Firm* — MEDLER FERRO WOODHOUSE & MILLS PLLC

(57) ABSTRACT

A crimper configured to radially compress a transcatheter valve prosthesis into a crimped configuration for delivery within a vasculature. The transcatheter valve prosthesis includes a frame and at least one leaflet secured within the frame. The crimper is configured to apply pressurized fluid to the at least one leaflet of the transcatheter valve prosthesis during the crimping process to prevent protrusion of the leaflet into the frame of the transcatheter valve prosthesis that may cause leaflet pinching and damage. The crimper
(Continued)

includes a plurality of crimper elements that collectively define a crimper chamber of the crimper, and at least one crimper element of the plurality of crimper elements includes an integral channel extending therethrough for applying the pressurized fluid to the at least one leaflet.

20 Claims, 24 Drawing Sheets

(58) Field of Classification Search
USPC .......................................................... 29/516
See application file for complete search history.

(56) References Cited

U.S. PATENT DOCUMENTS

| | | | | |
|---|---|---|---|---|
| 2005/0154450 | A1 | 7/2005 | Larson et al. | |
| 2006/0288561 | A1* | 12/2006 | Roach | A61F 2/9524 29/508 |
| 2007/0061009 | A1* | 3/2007 | Spenser | A61F 2/2412 623/2.11 |

* cited by examiner

CRIMPER WITH CHANNELS FOR APPLYING FLUID TO LEAFLETS OF A VALVE PROSTHESIS DURING CRIMPING

CROSS-REFERENCE TO RELATED APPLICATIONS

This application is a national stage entry of PCT/IB2023/050841, filed Jan. 31, 2023, which claims priority to U.S. Patent Application No. 63/306,228, filed Feb. 3, 2022, each of which is incorporated by reference herein in its entirety.

FIELD OF THE INVENTION

The present invention relates to a crimper configured to manage the folding of leaflets of a transcatheter valve prosthesis during the crimping process.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses are delivered in a radially compressed or crimped configuration so that the valve prosthesis can be advanced through the patient's vasculature. Once positioned at the treatment site, the valve prosthesis is expanded to engage tissue at the diseased heart valve region to, for instance, hold the valve prosthesis in position.

The present disclosure relates to improvements in radially compressing or crimping a valve prosthesis to ensure that the leaflets of the valve prosthesis are not pinched or damaged during the crimping process.

BRIEF SUMMARY OF THE INVENTION

According to a first embodiment hereof, the present disclosure provides an assembly including a transcatheter valve prosthesis and a crimper. The transcatheter valve prosthesis includes a frame and a valve component including at least one leaflet disposed within and secured to the frame. The transcatheter valve prosthesis has a crimped configuration for delivery within a vasculature and an expanded configuration for deployment within a native heart valve. The crimper is configured to radially compress the transcatheter valve prosthesis into the crimped configuration. The crimper is also configured to apply pressurized fluid in a radial direction to the at least one leaflet of the transcatheter valve prosthesis to displace the at least one leaflet radially inwards when the crimper is radially compressing the transcatheter valve prosthesis.

In an aspect of the first embodiment, and in combination with any other aspects herein, the disclosure provides that the crimper includes a plurality of crimper elements that collectively define a crimper chamber of the crimper. At least one crimper element of the plurality of crimper elements includes an integral channel extending therethrough for applying the pressurized fluid to the at least one leaflet.

In an aspect of the first embodiment, and in combination with any other aspects herein, the disclosure provides that the integral channel extends from an inlet to an outlet, the inlet being formed at a first end of the at least one crimper element and the outlet being formed at a second end of the at least one crimper element, the second end opposing the first end.

In an aspect of the first embodiment, and in combination with any other aspects herein, the disclosure provides that the at least one crimper element includes a first end and a second end, the second end opposing the first end. The integral channel extends from an inlet to an outlet, each of the inlet and the outlet being formed closer to the second end than the first end of the at least one crimper element.

In an aspect of the first embodiment, and in combination with any other aspects herein, the disclosure provides that one or more loops are attached to an exterior surface of the least one crimper element, the one or more loops being configured to receive a tubing component therethrough.

In an aspect of the first embodiment, and in combination with any other aspects herein, the disclosure provides that the at least one crimper element includes a first end and a second end, the second end opposing the first end and the second end including an exterior surface that defines a portion of the crimper chamber of the crimper. A fluid path defined by the integral channel exits from the at least one crimper element at a non-perpendicular angle relative to the exterior surface of the second end.

In an aspect of the first embodiment, and in combination with any other aspects herein, the disclosure provides that the transcatheter valve prosthesis includes exactly three leaflets and the crimper includes exactly three crimper elements that each include an integral channel extending therethrough for applying the pressurized fluid.

According to a second embodiment hereof, the present disclosure provides a crimper for radially compressing a transcatheter valve prosthesis having at least one leaflet into the crimped configuration. The crimper includes a plurality of crimper elements that collectively define a crimper chamber of the crimper. At least one crimper element of the plurality of crimper elements includes an integral channel extending therethrough for applying pressurized fluid in a radial direction to the at least one leaflet of the transcatheter valve prosthesis to displace the at least one leaflet radially inwards when the crimper is radially compressing the transcatheter valve prosthesis.

In an aspect of the second embodiment, and in combination with any other aspects herein, the disclosure provides that the integral channel extends from an inlet to an outlet, the inlet being formed at a first end of the at least one crimper element and the outlet being formed at a second end of the at least one crimper element, the second end opposing the first end.

In an aspect of the second embodiment, and in combination with any other aspects herein, the disclosure provides that the at least one crimper element includes a first end and a second end, the second end opposing the first end. The integral channel extends from an inlet to an outlet, each of the inlet and the outlet being formed closer to the second end than the first end of the at least one crimper element.

In an aspect of the second embodiment, and in combination with any other aspects herein, the disclosure provides that one or more loops attached to an exterior surface of the least one crimper element, the one or more loops being configured to receive a tubing component therethrough.

In an aspect of the second embodiment, and in combination with any other aspects herein, the disclosure provides that the at least one crimper element includes a first end and a second end, the second end opposing the first end and the second end including an exterior surface that defines a portion of the crimper chamber of the crimper. A fluid path defined by the integral channel exits from the at least one crimper element at a non-perpendicular angle relative to the exterior surface of the second end.

In an aspect of the second embodiment, and in combination with any other aspects herein, the disclosure provides that the transcatheter valve prosthesis includes exactly three leaflets and the crimper includes exactly three crimper elements that each include an integral channel extending therethrough for applying the pressurized fluid.

According to a third embodiment hereof, the present disclosure provides a method of crimping a transcatheter valve prosthesis onto a delivery system. A transcatheter valve prosthesis is positioned into a crimper chamber of a crimper. The transcatheter valve prosthesis includes a frame and a valve component including at least one leaflet disposed within and secured to the frame. The transcatheter valve prosthesis is in an expanded configuration. The crimper is operated to radially compress the transcatheter valve prosthesis into a crimped configuration for delivery within a vasculature. The crimper applies pressurized fluid in a radial direction to at least one leaflet of the transcatheter valve prosthesis to displace the at least one leaflet radially inwards when the crimper is radially compressing the transcatheter valve prosthesis.

In an aspect of the third embodiment, and in combination with any other aspects herein, the disclosure provides that the transcatheter valve prosthesis is partially compressed or fully compressed during the operating step.

In an aspect of the third embodiment, and in combination with any other aspects herein, the disclosure provides that the crimper includes a plurality of crimper elements that collectively define a crimper chamber of the crimper. At least one crimper element of the plurality of crimper elements includes an integral channel extending therethrough for applying the pressurized fluid to the at least one leaflet.

In an aspect of the third embodiment, and in combination with any other aspects herein, the disclosure provides that the step of operating the crimper includes reducing a volume of the crimper chamber of the crimper by causing the plurality of crimper elements to move radially inwards.

In an aspect of the third embodiment, and in combination with any other aspects herein, the disclosure provides that the integral channel extends from an inlet to an outlet, the inlet being formed at a first end of the at least one crimper element and the outlet being formed at a second end of the at least one crimper element, the second end opposing the first end.

In an aspect of the third embodiment, and in combination with any other aspects herein, the disclosure provides that the at least one crimper element includes a first end and a second end, the second end opposing the first end. The integral channel extends from an inlet to an outlet, each of the inlet and the outlet being formed closer to the second end than the first end of the at least one crimper element.

In an aspect of the third embodiment, and in combination with any other aspects herein, the disclosure provides that the transcatheter valve prosthesis includes exactly three leaflets and the crimper includes exactly three crimper elements that each include an integral channel extending therethrough for applying the pressurized fluid.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings may not be to scale.

DETAILED DESCRIPTION

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device. The following detailed description is merely exemplary in nature and is not intended to limit the invention of the application and uses of the invention. Furthermore, there is no intention to be bound by any expressed or implied theory presented in the preceding field of the invention, background, summary or the following detailed description.

Systems and methods of the disclosure include relate to a crimper configured for radially compressing a transcatheter valve prosthesis into a crimped configuration for delivery within a vasculature. More particularly, the crimper is configured to apply or deliver fluid to the leaflets of a transcatheter valve prosthesis during the crimping process to prevent protrusion of the leaflets into the frame of the transcatheter valve prosthesis that may cause leaflet pinching and damage. The detailed description hereof first includes a description of an exemplary prosthetic heart valve in FIGS. 1A-1B that may be used in embodiments hereof. The detailed description hereof also includes an illustration of the prosthetic heart valve of FIGS. 1A-1B disposed within a crimper configured to apply fluid to the leaflets thereof during the crimping process in FIGS. 2A-2B. FIGS. 3-11D further describe the crimper in more detail, and FIG. 12 illustrates another embodiment of a crimper configured to apply fluid to the leaflets thereof during the crimping process.

Figure 1A:
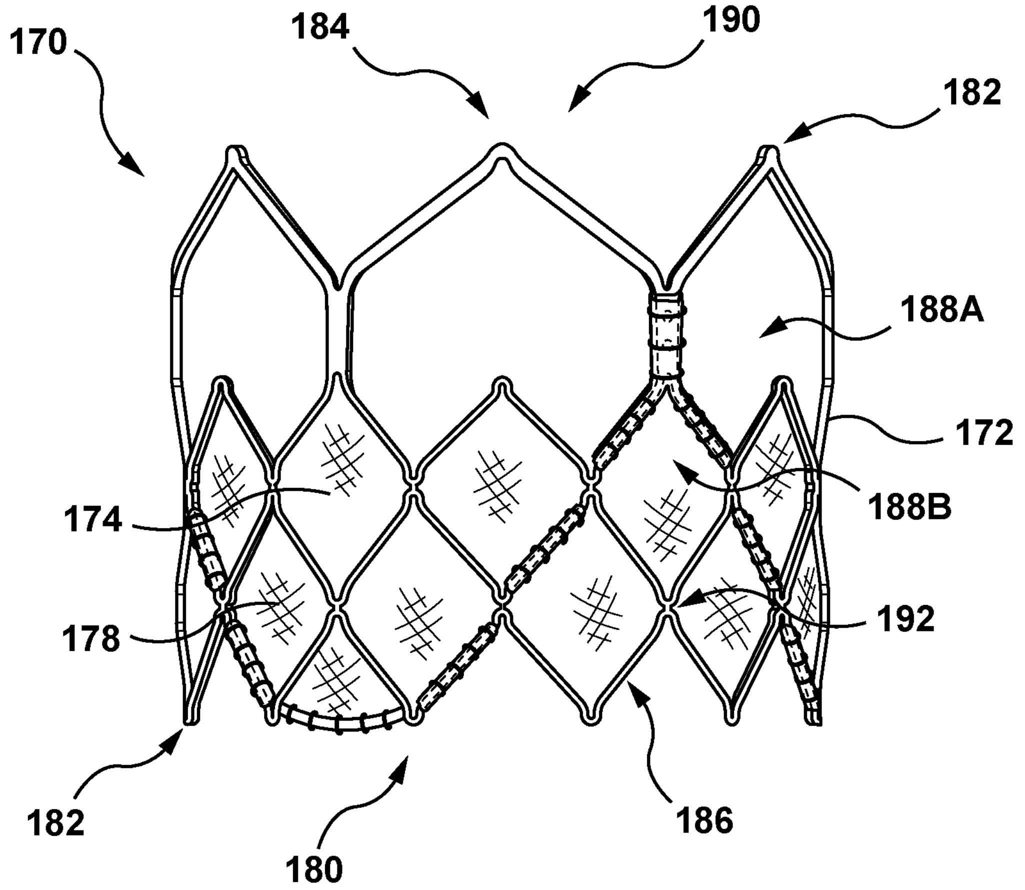
FIG. 1A shows a side view of a transcatheter valve prosthesis according to embodiments thereof.
Figure 1B:
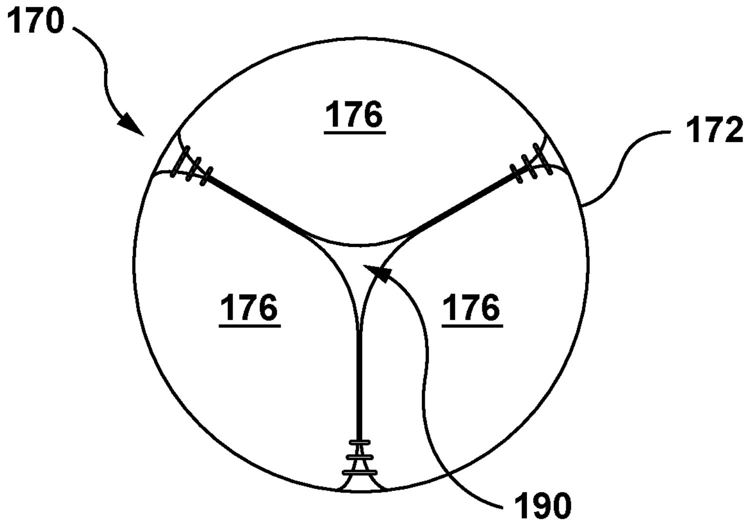
FIG. 1B shows a top view of the transcatheter valve prosthesis of FIG. 1A.

FIGS. 1A and 1B illustrate a transcatheter valve prosthesis 170 that may be utilized with the embodiments of the crimper described herein. The transcatheter valve prosthesis 170 is illustrated herein in order to facilitate description of the present invention. The following description of the transcatheter valve prosthesis 170 is merely exemplary in nature and is not intended to limit the invention or the application and uses of the invention. It is understood that any number of alternate heart valve prostheses can be used with the crimpers and methods described herein. Other non-limiting examples of transcatheter heart valve prostheses that can be used with the crimpers described herein are described in U.S. patent application Ser. No. 17/186,485, filed Feb. 26, 2021, which is incorporated by reference herein in its entirety. Although the transcatheter valve prosthesis 170 is a balloon-expandable valve prosthesis configured for placement within an aortic heart valve, embodiments of the crimpers described herein may be utilized with any transcatheter valve prosthesis that is crimped onto a delivery system. For example, embodiments of the crimpers described herein may be utilized with a transcatheter heart valve configured for placement within a pulmonary, aortic, mitral, or tricuspid valve, or may be utilized with a transcatheter valve prosthesis configured for placement within a venous valve or within other body passageways where it is deemed useful. There is no intention to be bound by any expressed or implied theory presented in the preceding technical field, background, brief summary or the following detailed description.

FIGS. 1A and 1B illustrate side and top views, respectively, of the transcatheter valve prosthesis 170. The transcatheter valve prosthesis 170 includes a radially-expandable frame 172 and a valve component 174. The frame 172 of the transcatheter valve prosthesis 170 is a unitary stent or scaffold that supports the valve component 174 within the interior of the frame 172. In an embodiment, the frame 172 is balloon-expandable. The valve component 174 includes at least one leaflet 176 disposed within and secured to the frame 172. In an embodiment, the valve component 174 of the transcatheter valve prosthesis 170 includes exactly three leaflets 176, as shown in FIG. 1B. The valve component 174 of the transcatheter valve prosthesis 170 is capable of blocking flow in one direction to regulate flow there-through via the valve leaflets 176. The transcatheter valve prosthesis 170 has a crimped configuration for delivery within a vasculature and an expanded configuration (as shown in FIGS. 1A and 1B) for deployment within a native heart valve.

The frame 172 is configured to secure the transcatheter valve prosthesis 170 in place in the vasculature of the patient. As shown in FIG. 1A, the transcatheter valve prosthesis 170 includes an inflow portion 180 and an outflow portion 184. The frame 172 of the transcatheter valve prosthesis 170 includes a plurality of struts 186 that are arranged to form a plurality of side openings or cells 188A, 188B arranged circumferentially around a longitudinal axis of the transcatheter valve prosthesis 170 and longitudinally to form a tubular structure defining a central lumen 190 of the transcatheter valve prosthesis 170. The struts 186 are defined as the straight segments of the frame 172. Two struts 186 come together to form a crown 182 and four struts 186 come together to form a node 192, as can be seen in FIG. 1A.

The inflow portion 180 of the transcatheter valve prosthesis 170 includes a plurality of crowns 182 with each crown 182 being formed between a pair of adjacent struts 186. Similarly, the outflow portion 184 of the transcatheter valve prosthesis 170 includes a plurality of crowns 182 with each crown 182 being formed between a pair of adjacent struts 186. The inflow portion 180 of the frame 172 includes a plurality of cells 188B defined as the spaces between the plurality of crowns 182, the plurality of nodes 192 and the plurality of struts 186. In an embodiment, the plurality of cells 188B may be diamond-shaped, as shown in FIG. 1A. In the embodiment described herein, the plurality of cells 188A located at the outflow portion 184 are heart-shaped and are relatively larger than the plurality of cells 188B located at the inflow portion 180 of the frame 172 to improve access to the coronary arteries. More particularly, the cells 188A located at the outflow portion 184 are configured to be of sufficient size to be easily crossed with a coronary guide catheter into either the right coronary artery or the left main coronary artery once the transcatheter valve prosthesis 170 is deployed in situ.

The valve component 174 of the transcatheter valve prosthesis 170 is capable of regulating flow therethrough via valve leaflets 176 that may form a replacement valve. FIGS. 1A and 1B illustrate an exemplary valve component 174 having three leaflets 176, although a single leaflet or bicuspid leaflet configuration may alternatively be used in embodiments hereof. When deployed in situ, the valve component 174 in a closed state is configured to block blood flow in one direction to regulate blood flow through the central lumen 190 of the frame 172 of the transcatheter valve prosthesis 170. FIG. 1A depicts a side view of the transcatheter valve prosthesis 170, wherein the valve component 174 is shown disposed within and secured to the frame 172 of the valve prosthesis 170. FIG. 1B depicts an atrial or inflow end view of the transcatheter valve prosthesis 170 shown in FIG. 1A. The valve leaflets 176 open during diastole.

Leaflets 176 may be attached to a graft material or skirt 178 which encloses or lines a portion of the frame 172 as would be known to one of ordinary skill in the art of prosthetic tissue valve construction, for example, using sutures or a suitable biocompatible adhesive. Leaflets 176 are sutured or otherwise securely and sealingly attached along their bases to the interior surface of the graft material, or otherwise attached to the frame 172. Adjoining pairs of leaflets are attached to one another at their lateral ends to form commissures, with free edges of the leaflets 176 forming coaptation edges that meet in a closed configuration. The orientation of the leaflets 176 within the valve component 174 depends upon on which end of the transcatheter valve prosthesis 170 is the inflow end 180 and which end of the transcatheter valve prosthesis 170 is the outflow end 184, thereby ensuring one-way flow of blood through the transcatheter valve prosthesis 170.

The valve leaflets 176 and skirt 178 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

As shown in FIGS. 1A and 1B, the valve component 174 includes at least one leaflet 176 disposed within and secured to the frame 172 of the transcatheter valve prosthesis 170. A crimper may be used to radially compress the transcatheter valve prosthesis 170 from an expanded configuration to a crimped configuration for delivery within a vasculature. During the crimping process, radial compression exerted by the crimper causes the area of the cells 188A, 188B of the frame 172 to decrease. In some instances, the at least one leaflet 176 of the valve component 174 may protrude through the cells 188A at the outflow portion 184 of the frame 172 during the process, which may cause the at least one leaflet 176 to get pinched between struts 186 of the frame 172 and sustain damage. Leaflet protrusion becomes increasingly likely as the area of the cells increase and/or in view of higher crimping forces that are needed to crimp balloon expandable implants.

Figure 2B:
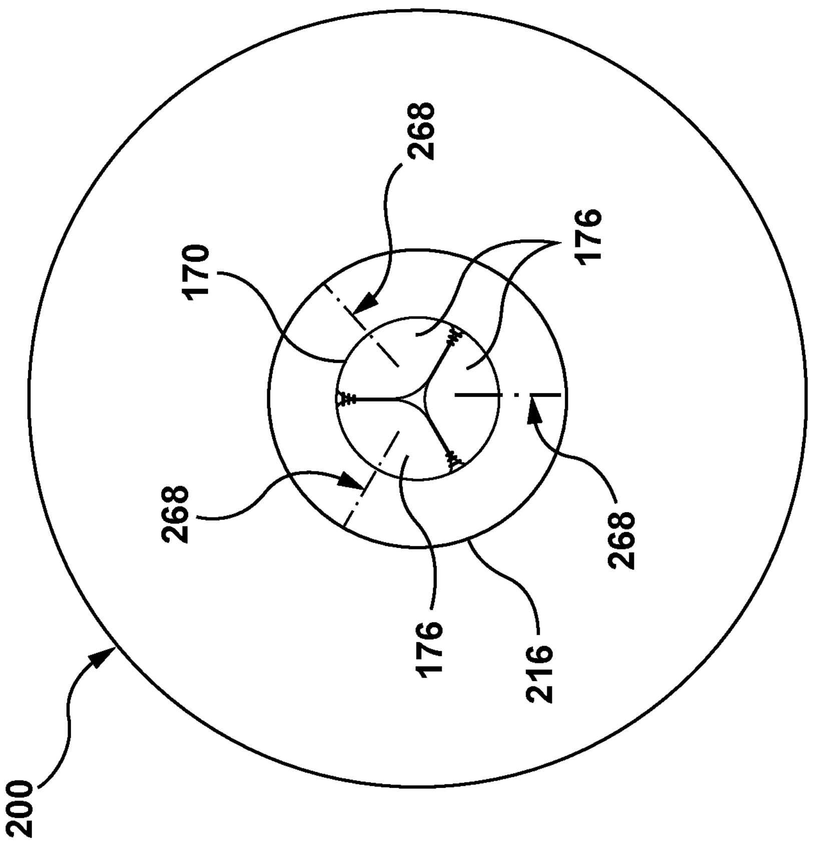
FIG. 2B shows a schematic front view of the interior of the crimper of FIG. 2A.
Figure 2A:
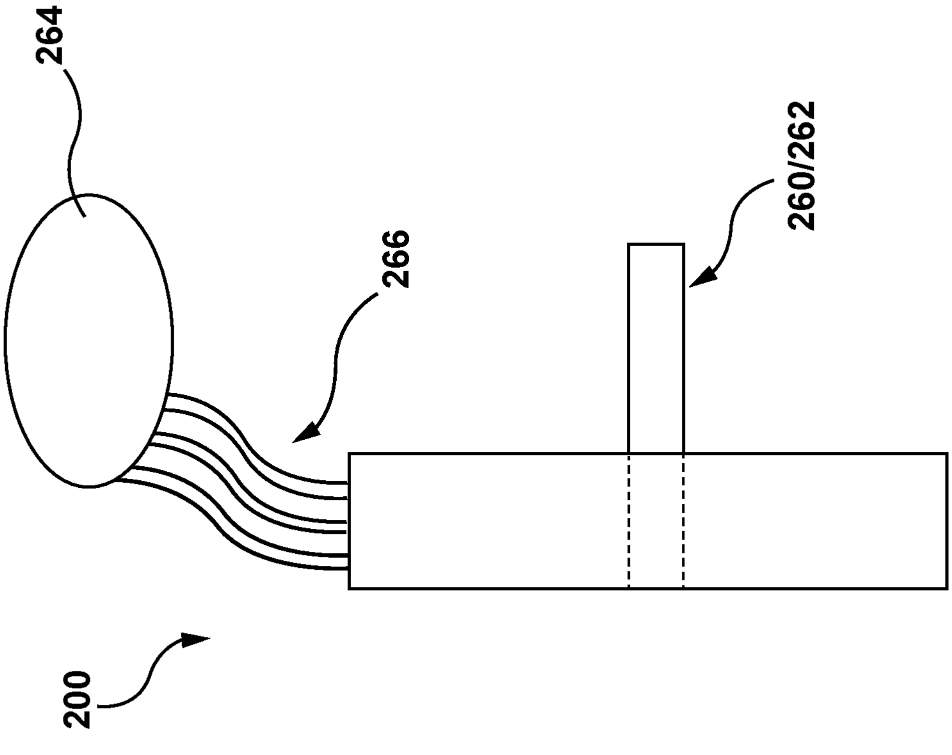
FIG. 2A shows a schematic side view of an assembly according to embodiments thereof, the assembly including a crimper, a balloon catheter, a fluid source, and a plurality of tubing components, wherein the crimper is configured for applying fluid to leaflets of the transcatheter valve prosthesis during crimping.

FIG. 2A is a schematic illustration of an assembly including a crimper 200 according to an embodiment hereof and a delivery system 260 including a shaft 262 during the crimping procedure according to embodiments hereof. The crimper 200 is configured for use with a transcatheter valve prosthesis, such as but not limited to the transcatheter valve prosthesis 170 described herein, when radially compressing the transcatheter valve prosthesis into a crimped configuration for delivery within a vasculature. For illustrative purposes only, the crimper 200 will be described for use with the transcatheter valve prosthesis 170 since the structure thereof has been described herein.

The crimper 200 is configured to deliver or provide pressurized fluid to the leaflets 176 of the transcatheter valve prosthesis 170 during the crimping process in order to prevent and/or minimize leaflet protrusion. More particularly, the crimper 200 is configured to receive a plurality of tubing components 266 that each extend between a fluid source 264 and an interior of the crimper 200 such that the fluid source 264 may provide pressurized fluid into the crimper 200. The term "fluid" as used herein includes gases (i.e., air) as well as liquids such as water, saline, and the like. In an embodiment, the fluid is pressurized with a pressure between 1 PSI and 10 PSI. However, this is not meant to be limiting and it should be understood that the fluid being applied by the crimper to the at least one leaflet of the transcatheter valve prosthesis is not required to be pressurized. In an embodiment, the fluid source 264 is chilled and also functions to chill the frame 172 of the transcatheter valve prosthesis 170 during the crimping process, which may be formed from Nitinol, in addition to radially displacing the leaflets 176 of the transcatheter valve prosthesis 170 during the crimping process.

Figure 2C:
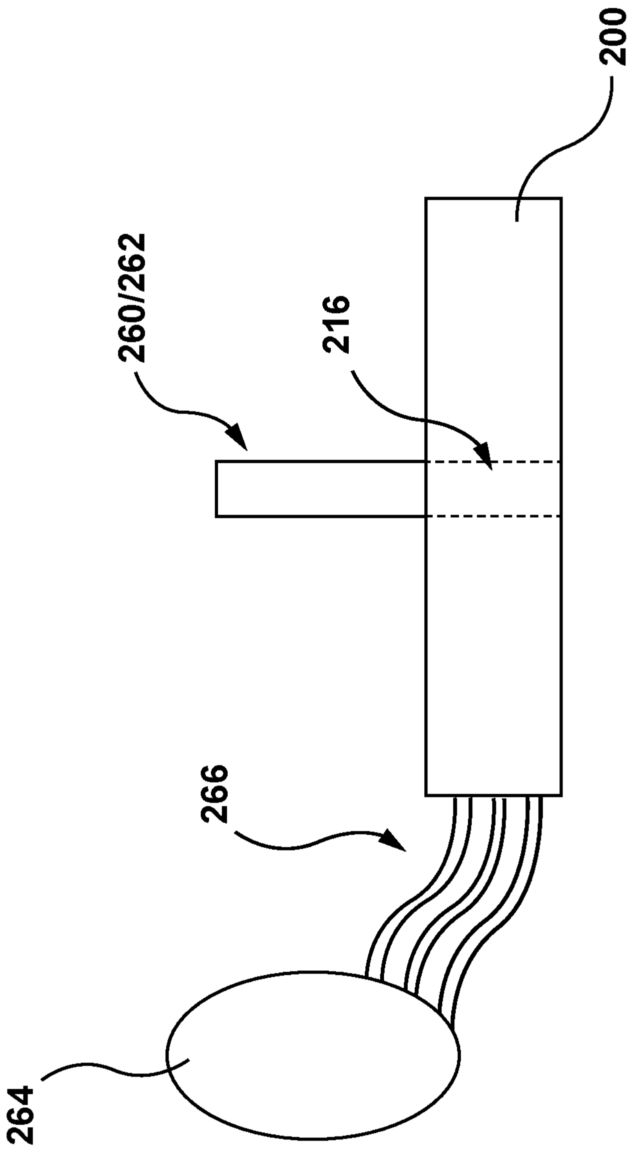
FIG. 2C shows a schematic side view of the assembly of FIG. 2A in an alternative orientation.

In an embodiment, the crimper 200 is an iris-style crimper that includes crimper elements 314A, 314B (not shown in FIG. 2; best shown on FIG. 4), which are collectively referred to herein as crimper elements 314 and which collectively define the crimper chamber 216, with each of the crimper elements 314 including a surface that forms a portion of the crimper chamber 216. Fluid from the fluid source 264 is directed through one or more crimper elements 314B of the crimper 200 towards the leaflets 176 of the transcatheter valve prosthesis 170. The fluid is applied to an exterior surface of each leaflet 176 of the transcatheter valve prosthesis 170 such that the fluid pushes the leaflets 176 radially inwards. Displacing the leaflets 176 radially inwards during the crimping process minimizes risk of leaflet protrusion (through the frame 172 of the prosthesis 170) and damage.

Since the transcatheter valve prosthesis 170 includes exactly three leaflets 176, the crimper 200 is configured to receive exactly three tubing components 266. Each tubing component 266 is configured to be coupled to a crimper element 314B such that exactly three crimper elements are configured to receive the fluid from a respective tubing component 266. The exactly three crimper elements 314B are equally and circumferentially spaced apart from each other, and are spaced to align with the three leaflets 176 of the transcatheter valve prosthesis 170. It will be apparent to one of ordinary skill in the art that the number of tubing components and respective fluid paths therefrom may vary depending on the number of leaflets of the transcatheter valve prosthesis being crimped. In addition, although the crimper 200 as described herein includes exactly three crimper elements 314B configured to receive the fluid from a respective tubing component 266, a greater or lesser number of crimper elements may be configured to receive the fluid from a respective tubing component 266. For example, it may be desirable for two or three crimper elements to deliver fluid to a single leaflet of a transcatheter valve prosthesis.

The dotted lines in FIG. 2B represent a plurality of fluid paths 268 within the crimper chamber 216 of the crimper 200 such that the fluid is directed to and aimed at the three leaflets 176 of the transcatheter valve prosthesis 170. Each fluid path 268 is aligned with a center of each leaflet 176 such that when the pressurized fluid is applied, each leaflet 176 is held in a substantially closed state when the crimper 200 is radially compressing the transcatheter valve prosthesis 170 into a partially crimped configuration or the crimped configuration. In this embodiment, the three fluid paths 268 are equally and circumferentially spaced apart from each other, as can be seen in FIG. 2B. The term "substantially closed state" is used herein to describe the leaflets 176 of the valve component 174 being positioned such that the free edges thereof abut against or contact the shaft 262 of the delivery system 260. The closed state of the leaflets 176 against the shaft 262 of the delivery system 260 is similar to the closed state of the leaflets 176 within the vasculature of the patient, in which the leaflets 176 are configured to block blood flow in one direction to regulate the blood flow through the central lumen 190 of the valve prosthesis 170, except that the shaft 262 of the delivery system 260 extends through the central lumen 190 of the valve prosthesis 170 during the crimping procedure. In another embodiment, when the pressurized fluid is applied, each leaflet 176 is displaced radially inward to prevent leaflet protrusion but does not abut against or contact the shaft 262 of the delivery system when the crimper 200 is radially compressing the transcatheter valve prosthesis 170 towards the crimped configuration.

With continued reference to FIGS. 2A and 2B, a method of using the crimper 200 during the crimping process of the transcatheter valve prosthesis 170 will now be described. The transcatheter valve prosthesis 170 is first loaded onto the balloon of the balloon catheter of the delivery system 260 in an expanded configuration. The assembly of the transcatheter valve prosthesis 170 and the delivery system 260 is then positioned within the crimper chamber 216 of the crimper 200. When the crimper 200 operates to radially compress the transcatheter valve prosthesis 170 into a crimped configuration, the crimper 200 applies pressurized fluid to the three leaflets 176 of the transcatheter valve prosthesis 170 to urge the leaflets 176 into a substantially closed state during the crimping process. The fluid is applied radially to an exterior surface of the leaflets 176 of the transcatheter valve prosthesis 170 such that the fluid pushes the leaflets 176 radially inwards. Displacing the leaflets 176 radially inwards during the crimping process minimizes the risk of leaflet protrusion and damage. When fluid is applied to the leaflets 176, pooling of the fluid may occur on or around the leaflets 176 of the valve component 174. Such pooling can be beneficial to displacing the leaflets 176 radially inwards. When the transcatheter valve prosthesis 170 is fully crimped onto the delivery system 260, the assembly of the transcatheter valve prosthesis 170 and the delivery system 260 may be removed from the crimper chamber 216 of the crimper 200.

In the embodiment of FIG. 2A, the crimper 200 is oriented such that the crimper chamber 216 (as well as the assembly of the transcatheter valve prosthesis 170 and the delivery system 260 placed therein) is oriented horizontally. In another embodiment depicted in FIG. 2C, the crimper 200 is oriented such that the crimper chamber 216 (as well as the assembly of the transcatheter valve prosthesis 170 and the delivery system 260 placed therein) is oriented vertically. The vertical orientation of the crimper chamber 216 allows or permits gravity to assist the fluid in urging the leaflets 176 into a substantially closed state during the crimping process.

The crimper 200 will now be described in greater detail with references to FIGS. 3-11D. As previously stated, the crimper 200 is an iris-style crimper that includes a plurality of crimper elements 314 which define the crimper chamber 216, with each of the crimper elements 314 including a surface that forms a portion of the crimper chamber 216. A volume of the crimper chamber 216 is decreased in order to radially compress the transcatheter valve prosthesis 170 into a crimped configuration on the delivery system 260. It should be understood that the crimper 200 described herein is merely exemplary in nature and is not intended to limit the invention or the application and uses of the invention. It is understood that alternate crimpers may be modified to be configured to deliver fluid during the crimping process. Other non-limiting examples of crimpers that may be modified to be configured to deliver fluid during the crimping process are described in U.S. application Ser. No. 17/394,025, filed Aug. 4, 2021, which is incorporated by reference herein in its entirety.

The crimper 200 operates to convert the transcatheter valve prosthesis 170 from its uncompressed state to its compressed state. In operation, the transcatheter valve prosthesis 170 is loaded into the crimper chamber 216. One skilled in the art will realize that the dimension of the crimper chamber 216 can be changed to create a different volume as required by the transcatheter valve prosthesis 170 being compressed and positioned. The delivery device 260 and the transcatheter valve prosthesis 170 can be positioned and aligned relative to the transcatheter valve prosthesis 170. The crimper 200 is then moved from the open state to the closed state to convert the transcatheter valve prosthesis 170 from its uncompressed state to its compressed state and load the transcatheter valve prosthesis 170 onto the delivery device 260. As the crimper elements 314 move radially inward, the space available for the crimper elements 314 to occupy reduces and therefore the space between the crimper elements 314 reduces. As such, the volume of the crimper chamber 216 decreases and the crimper elements 314 apply a compression force to external surfaces of the transcatheter valve prosthesis 170 to crimp the transcatheter valve prosthesis 170 from an uncompressed or radially expanded state to a radially compressed state. The operation of the crimper 200 is explained in further detail below with reference to FIGS. 11A-11D.

Figure 3:
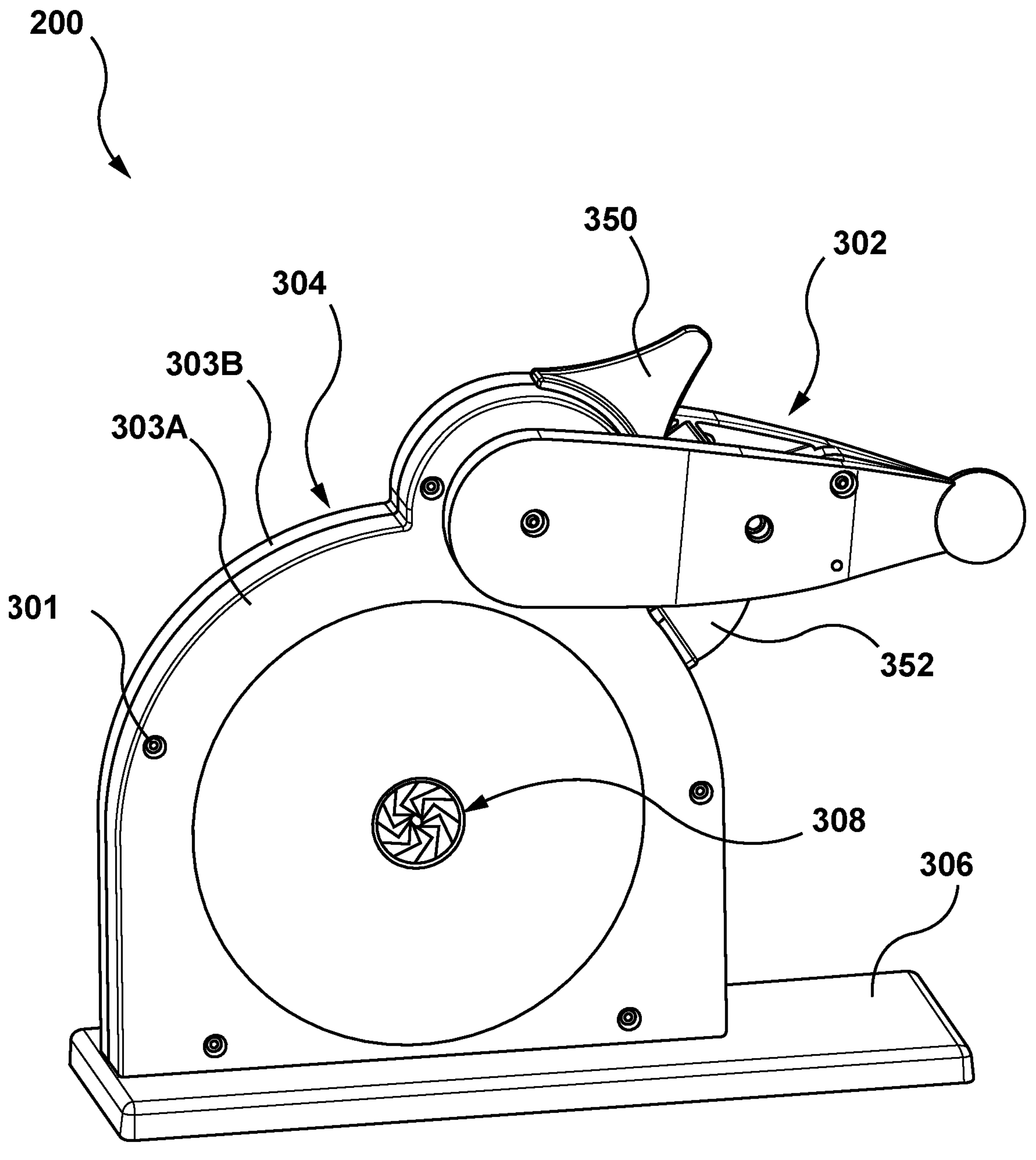
FIGS. 3 and 4 depict different views of a crimper according to an embodiment hereof.

FIG. 3 is a perspective view of the crimper 200. As illustrated in FIG. 3, the crimper 200 includes a handle 302, a crimper housing 304, and a base 306. The crimper housing 304 includes a first side 303A and a second side 303B positioned opposite the first side 303A. The first side 303A of the crimper housing 304 is coupled to the second side 303B of the crimper housing 304 by one or more connectors 301. The connectors 301 can be any type of device to couple the first side 303A of the crimper housing 304 to the second side 303B of the crimper housing 304 such as a bolt, screw, pin, snap-fit features, and similar mechanical components.

The crimper housing 304 includes an opening 308 that extends therethrough or from the first side 303A of the crimper housing 304 to the second side 303B of the crimper housing 304. In an embodiment, the opening 308 is formed in an approximate circular cross-sectional shape. The opening 308 allows access to the crimper chamber 216 of the crimper 200.

The base 306 provides a stable platform for operating the crimper 200 during crimping procedures. The crimper housing 304 is attached or fixed to the base 306 by one or more connection devices 320 (shown in FIG. 4). The connection devices 320 can be any type of device to couple the crimper housing 304 to the base 306 such as a bolt, screw, pin, snap-fit features, and similar mechanical components.

The crimper 200 also includes a first stop 350 and a second stop 352. The first stop 350 and the second stop 352 each provide a surface that stops the movement of the handle 302 in the downward direction. The first stop 350 and the second stop 352 provide predetermined stop positions of the handle 302 that correspond to or result in a predetermined diameter of the crimper chamber 216. That is, the first stop 350 and the second stop 352 are physical stops to cause an implantable medical device to be compressed to a predetermined diameter or compression. The first stop 350 operates to allow the transcatheter valve prosthesis 170 to be partially compressed. Likewise, the second stop 352 operates to allow the transcatheter valve prosthesis 170 to be fully compressed. The first stop 350 and the second stop 352 can be removably coupled to the crimper housing 304. As such, the first stop 350 and/or the second stop 352 can be added and/or removed to allow a transcatheter valve prosthesis to be compressed to predetermined diameters.

Figure 4:
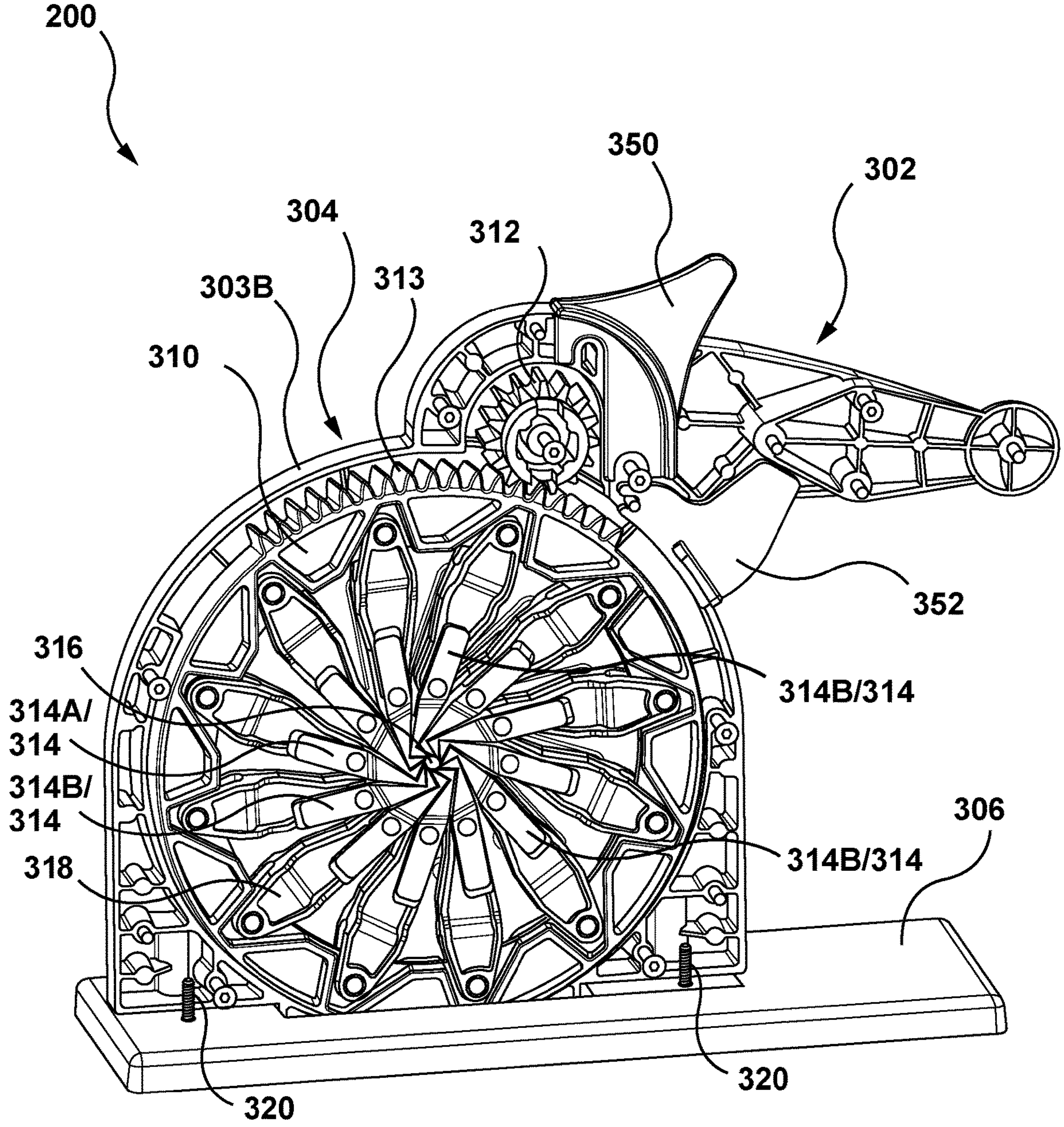

FIG. 4 illustrates a perspective view of the crimper 200 in which the first side 303A of the crimper housing 304 has been removed to illustrate internal components of the crimper 200. The crimper 200 includes a cam 310, a plurality of rods 318, and the plurality of crimper elements 314 that form the crimper chamber 216. The handle 302 is coupled to the cam 310 via a gear 312 as will be described in more detail herein. The cam 310 is coupled to the plurality of crimper elements 314 by the plurality of rods 318. To operate the crimper 200, a force is applied by a user to the handle 302 in the direction towards the base 306. Via the gear 312, the force applied to the handle 302 causes the gear 312 to rotate clockwise, which then causes the cam 310 to rotate in an opposing counter-clockwise direction. Rotation of the cam 310 causes the crimper elements 314 to move radially inward, as will be described in more detail herein.

Figure 5A:
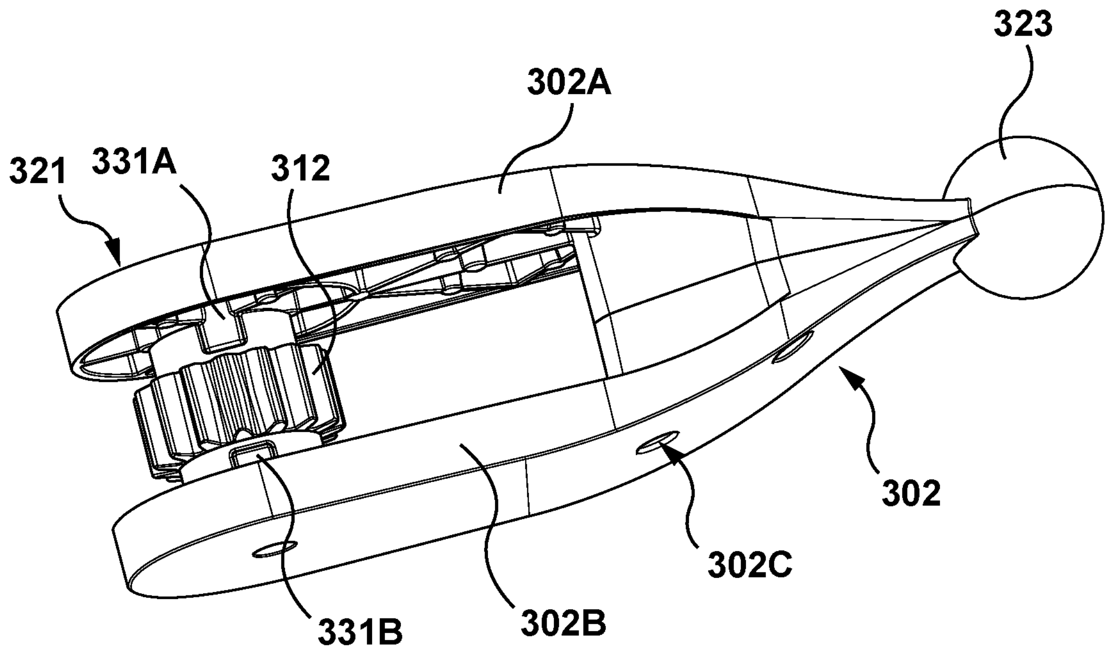
FIGS. 5A, 5B, and 5C depict perspective, side, and exploded views, respectively, of a handle and gear subassembly of the crimper of FIGS. 3 and 4.
Figure 5B:
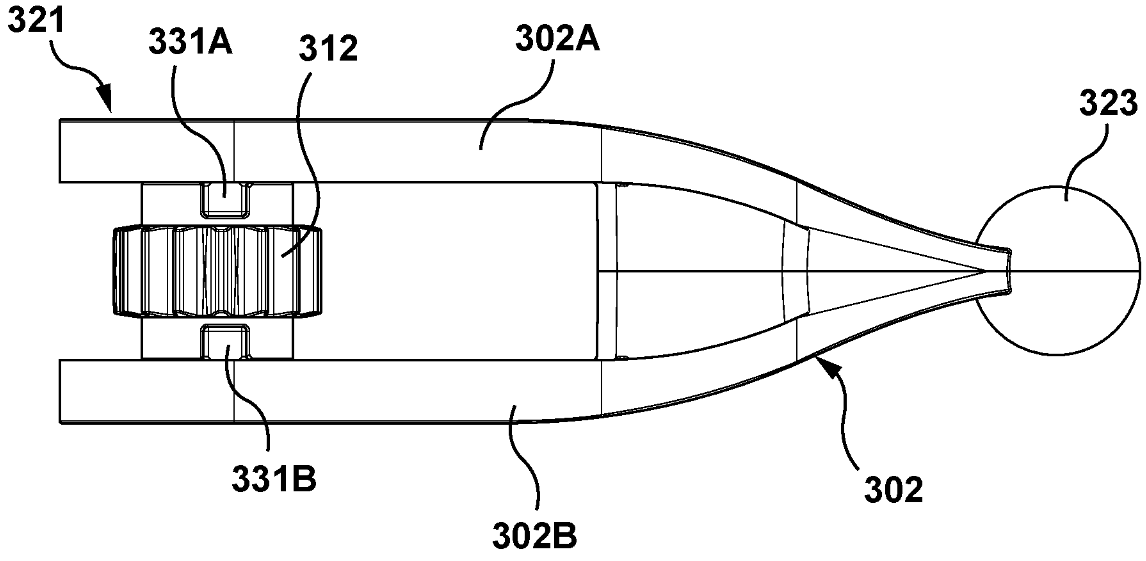
Figure 5C:
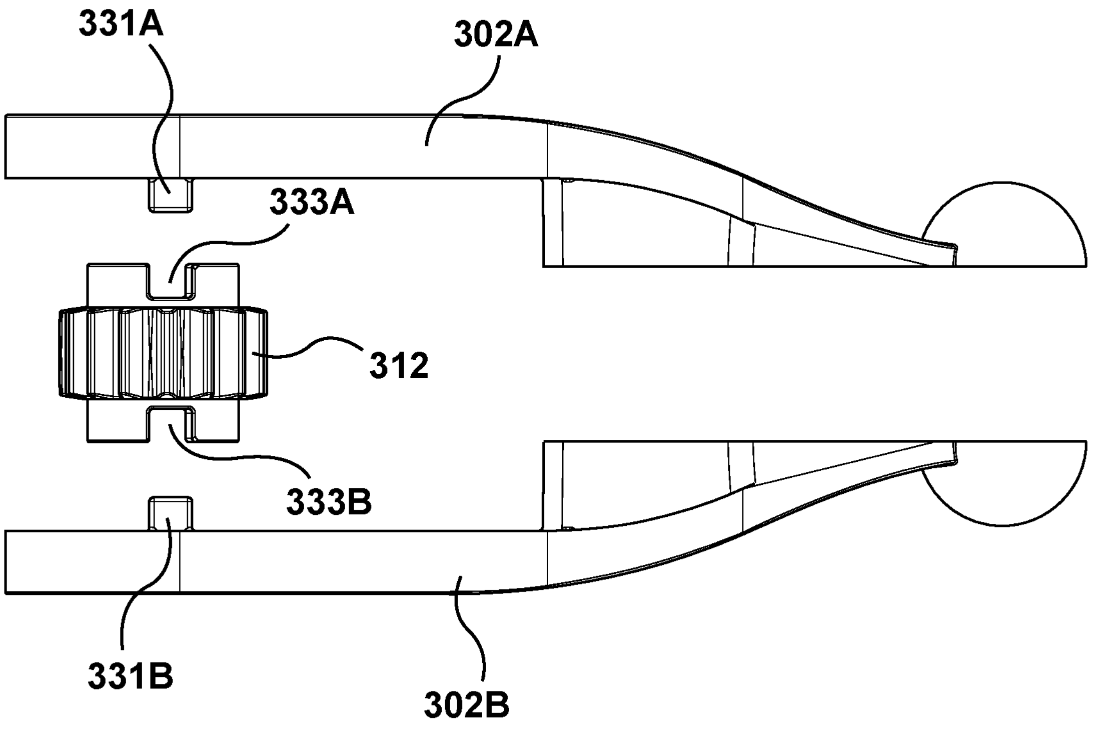

The internal components of the crimper 200 and their operation thereof will now be described in more detail herein. FIGS. 5A, 5B, and 5C depict perspective, side, and exploded views, respectively, of a subassembly of the handle 302 and the gear 312 of the crimper 200. The handle 302 is accessible to the user and is coupled to the crimper housing 304. The handle 302 includes a first side 302A and a second side 302B positioned opposite the first side 302A. The first side 302A of the handle 302 is formed as a "mirror" of the second side 302B of the handle 302 and is coupled to the second side 302B to collectively form the handle 302. The first side 302A of the handle 302 is coupled to the second side 302B of the handle 302 by one or more connectors 302C. The connectors 302C can be any type of device to couple the first side 302A of the handle 302 to the second side 302B of the handle 302 such as a bolt, screw, pin, and similar mechanical components. In addition, the first side 302A of the handle 302 is coupled to the second side 302B of the handle 302 by the gear 312 as will be described in more detail.

The handle 302 includes a first end 321 and a second or opposing end 323. The first end 321 of the handle 302 is coupled to the crimper housing 304, and the second end 323 is free or unattached to the crimper housing 304. At the first end 321 thereof, the first side 302A and the second side 302B are coupled to the crimper housing 304 and are coupled to the gear 312, which is disposed within the crimper housing 304. At the second end 323 thereof, the first side 302A and the second side 302B collectively have a rounded ball configuration for easy handling by the user during manipulation of the handle 302. When the handle 302 is rotated by the user for operation of the crimper 200, the user generally grasps or holds the second end 323 of the handle 302.

At the first end 321 thereof, the first side 302A and the second side 302B of the handle 302 are spaced apart such that a gap is formed therebetween, with the gap being sized and configured to receive the gear 312. On an interior surface of the first side 302A, a tab or protrusion 331A extends inward towards the second side 302B. Similarly, on an interior surface of the second side 302B, a tab or protrusion 33B extends inward towards the first side 302A. The tabs 331A, 331B are sized and configured to be received within a corresponding recess 333A, 333B, respectively, of the gear 312 to couple the first and second sides 302A, 302B to the gear 312. By forming the gear 312 and the handle 302 as separate components, the subassembly is stronger and is less prone to breakage. In addition, forming the gear 312 and the handle 302 as separate components simplifies the manufacturing thereof. The gear 312 is a cylindrical component having a plurality of teeth formed on circumferentially around an outer surface thereof. As will be described in more detail below, the gear 312 is configured to mate with a gear portion 313 of the cam 310. In other words, the gear 312 includes a plurality of teeth on an outer surface thereof that are sized and shaped to mate or mesh with the plurality of teeth of the gear portion 313 of the cam 310.

Figure 6A:
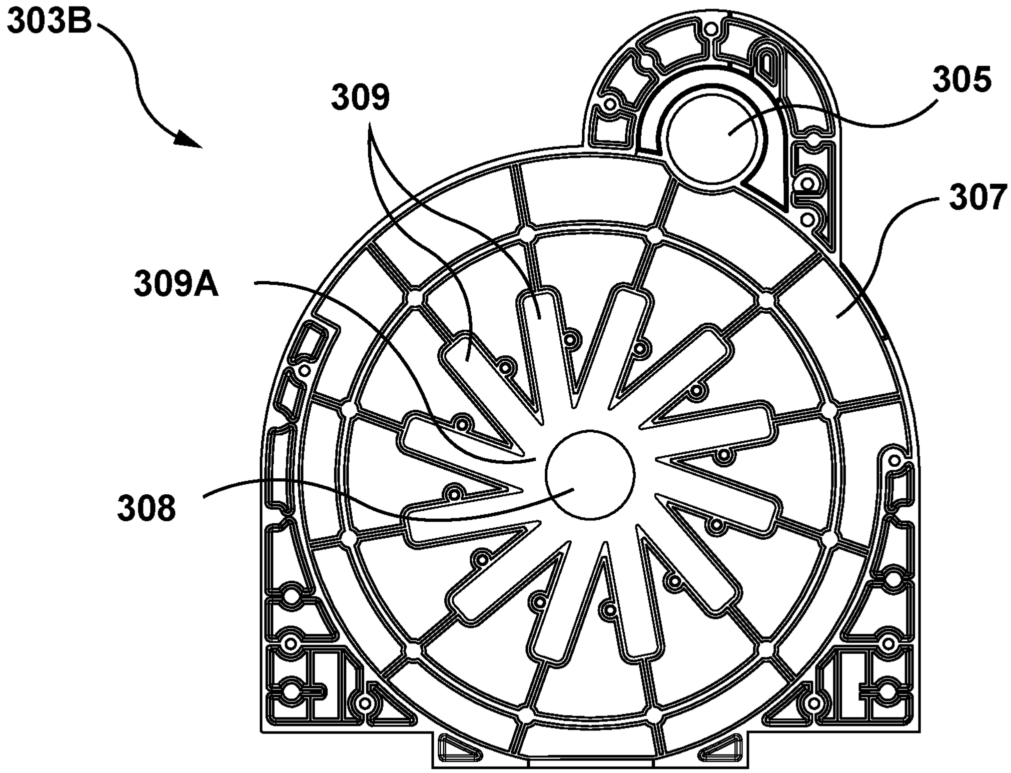
FIGS. 6A and 6B depict side and perspective views, respectively, of a side of a housing of the crimper of FIGS. 3 and 4.
Figure 6B:
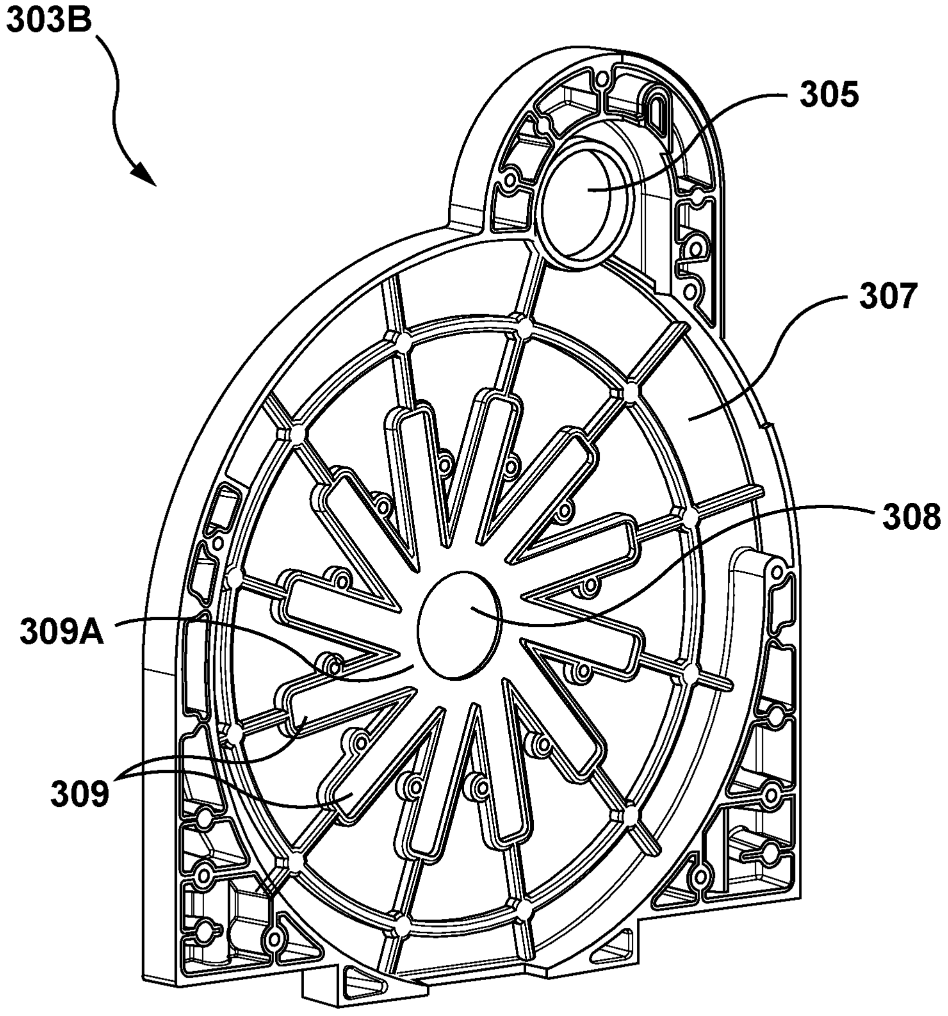

FIGS. 6A and 6B depict side and perspective views, respectively, of the second side 303B of the crimper housing 304. While the second side 303B of the crimper housing 304 is only discussed below, one skilled in the art will realize that the first side 303A of the crimper housing 304 include the same components as illustrated in FIGS. 6A and 6B. For example, the first side 303A of the crimper housing 304 is formed as a "mirror" of the second side 303B of the crimper housing 304 and is coupled to the second side 303B to collectively form the crimper housing 304.

The second side 303B of the crimper housing 304 includes an interior surface 307 and an opposing or exterior surface (not shown). The second side 303B includes the opening 308 which allows access to the crimper chamber 216 formed by the crimper elements 314. The second side 303B also includes a handle opening 305 that is formed therethrough and configured to receive the handle 302 therein. The handle opening 305 is also configured to receive the first stop 350 and the second stop 352. Crimper element channels 309 are formed on the interior surface 307 of the second side 303B. Each crimper element channels 309 may be formed as a generally rectangular groove or channel that extends inward from a midportion of the second side 303B towards the opening 308 in a generally radial direction. The crimper element channels 309 are formed in an arc around the second side 303B and are disposed at equal, circumferentially spaced-apart increments around the opening 308. A central annular cavity 309A is a circular groove or channel formed in the interior surface 307 of the second side 303B that surrounds or encircles the opening 308. The central annular cavity 309A has the same depth as the crimper element channels 309, and the crimper element channels 309 extend into or terminate at the central annular cavity 309A. Thus, the crimper element channels 309 and the central annular cavity 309A form a continuous groove or cavity formed in the interior surface 307 of the second side 303B.

The crimper element channels 309 and the central annular cavity 309A are configured to moveably secure the crimper elements 314 within the crimper housing 304. The crimper element channels 309 are formed with a width and depth to accommodate the crimper elements 314 when the second side 303B of the crimper housing 304 is mated with the first side 303A of the crimper housing 304. The crimper element channels 309 also function to limit the radially outward motion or travel of the crimper elements 314 in order to ensure that the crimper chamber 216 is not inadvertently over-opened. If the radially outward motion or travel of the crimper elements 314 is not restricted in any way, the crimper chamber 216 may be continually opened to a size or dimension in which portions of the crimper elements 314 no longer overlap, thereby resulting in gaps that could pinch and damage the implantable medical device disposed within the crimper chamber 216. Stated another way, the crimper element channels 309 are configured to set or limit a maximum diameter of the crimper chamber 216. In an embodiment, each crimper element channel 309 may be sized to limit the travel of the crimper elements 314 and thereby set or limit a maximum diameter of the crimper chamber 216. In another embodiment, at least one crimper element channel 309 is sized to limit travel of the crimper elements 314 and thereby set or limit a maximum diameter of the crimper chamber 216. In such an embodiment, the at least one crimper element channel is shorter than the remaining crimper element channels. In another embodiment, between two and six crimper element channels 309 may be sized to limit the travel of the crimper elements 314 and thereby set or limit a maximum diameter of the crimper chamber 216. In such an embodiment, the between two and six crimper element channels are shorter than the remaining crimper element channels.

Figure 7A:
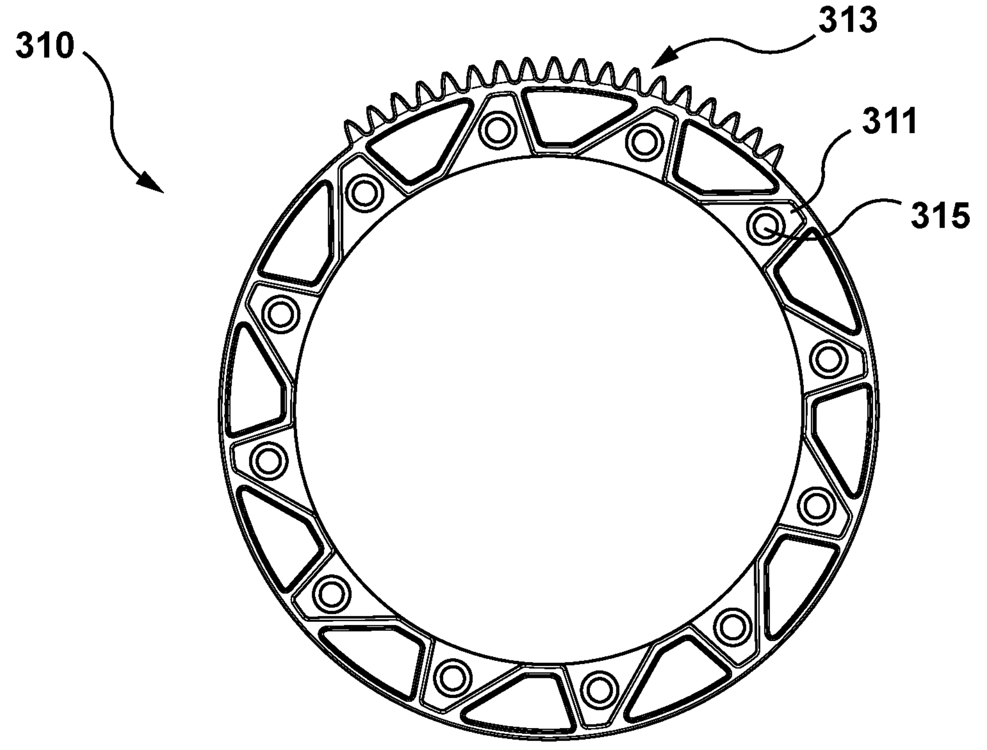
FIGS. 7A and 7B depict side and perspective views, respectively, of a cam of the crimper of FIGS. 3 and 4.
Figure 7B:
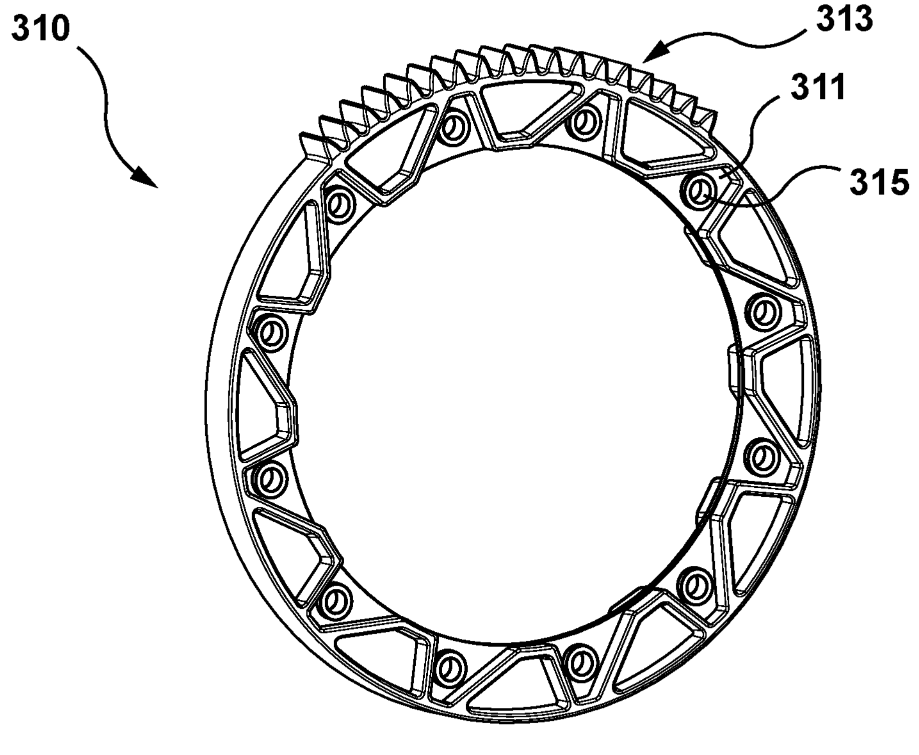

FIGS. 7A and 7B depict side and perspective views of the cam 310, according to an embodiment hereof. One skilled in the art will realize that FIGS. 7A and 7B illustrate one example of a cam and that existing components illustrated in FIGS. 7A and 7B may be removed and/or additional components may be added to the cam 310. The cam 310 is an annular element or circular ring that is disposed within the crimper housing 304.

The cam 310 operates to translate the rotational movement of the handle 302 to the crimper elements 314 via the rods 318. As the handle 302 moves, the cam 310 rotates and translates or transforms the rotational motion of the handle 302 into linear motion of the crimper elements 314 via the rods 318. The cam 310 includes an integrated plurality of teeth or gear portion 313 formed on an outer surface thereon. The gear portion 313 is configured to engage with the gear 312. More particularly, the plurality of teeth of gear portion 313 are sized and shaped to mesh or mate with the plurality of teeth of gear 312 so that rotation of gear 312 causes rotation of the cam 310. The gear portion 313 and the gear 312 have opposing orientations such that rotation of the gear 312 in a first direction causes rotation of the cam 310 in a second or opposing direction. When disposed within the crimper housing 304, the cam 310 is oriented such that gear portion 313 engages the gear 312, near the handle opening 305 of the crimper housing 304.

As illustrated in FIGS. 7A and 7B, the cam 310 includes a plurality of rod channels or grooves 311. Each of the rod channels 311 is configured to receive a rod 318. A connection hole 315 extends through the cam 310 and is disposed within each rod channel 311. Each connection hole 315 is configured to receive a pin (not shown) that couples the cam 310 to a rod 318 that is disposed within the rod channel 311. Stated another way, a plurality of pins are utilized to couple the cam 310 to the rods 318, with each pin passing through the connection hole 315 and passing through similar connection holes formed through the rod 318. For example, the pin can be a dowel pin, a bolt, and the like. The rod channel 311 is also configured to limit rotational movement of the rods 318, as described in more detail herein.

Figure 8A:
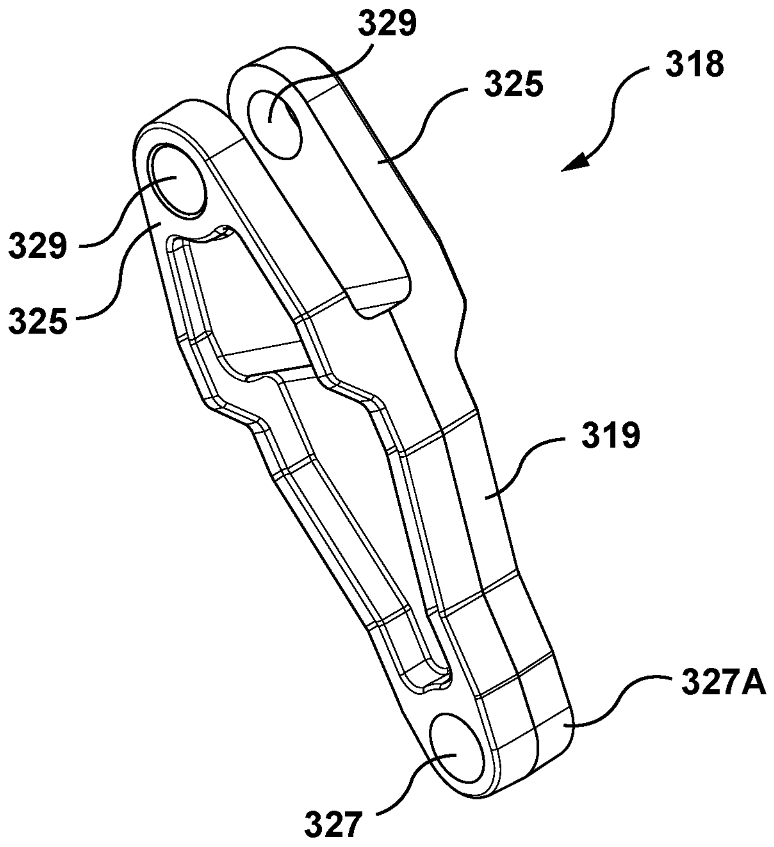
FIGS. 8A and 8B depict perspective and front views, respectively, of a rod of the crimper of FIGS. 3 and 4.
Figure 8B:
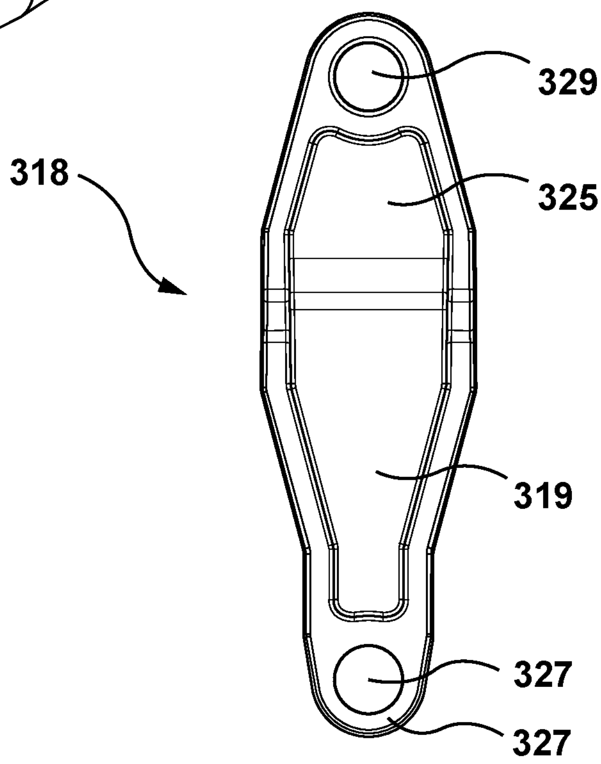
Figure 9A:
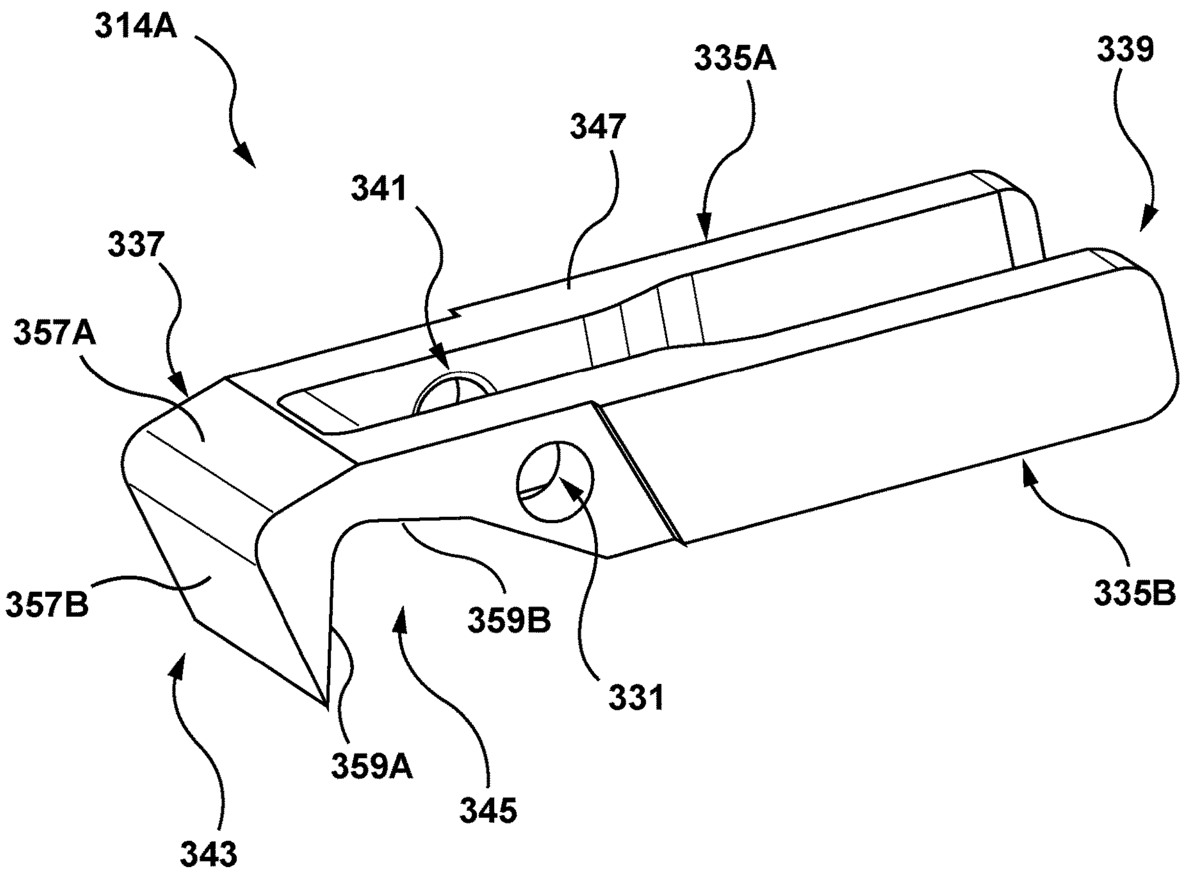
FIGS. 9A, 9B, 9C and 9D depict different views of a crimper element of the crimper of FIGS. 3 and 4.
Figure 9B:
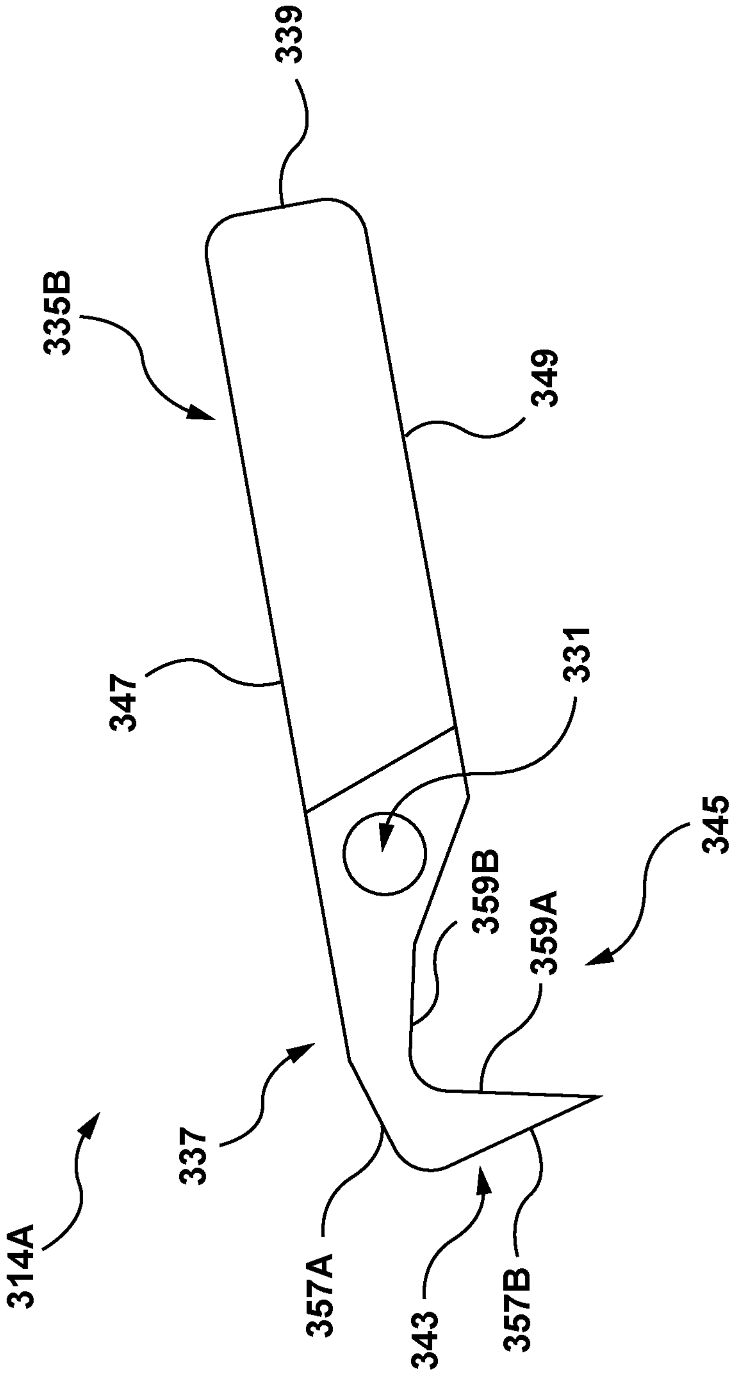
Figure 9C:
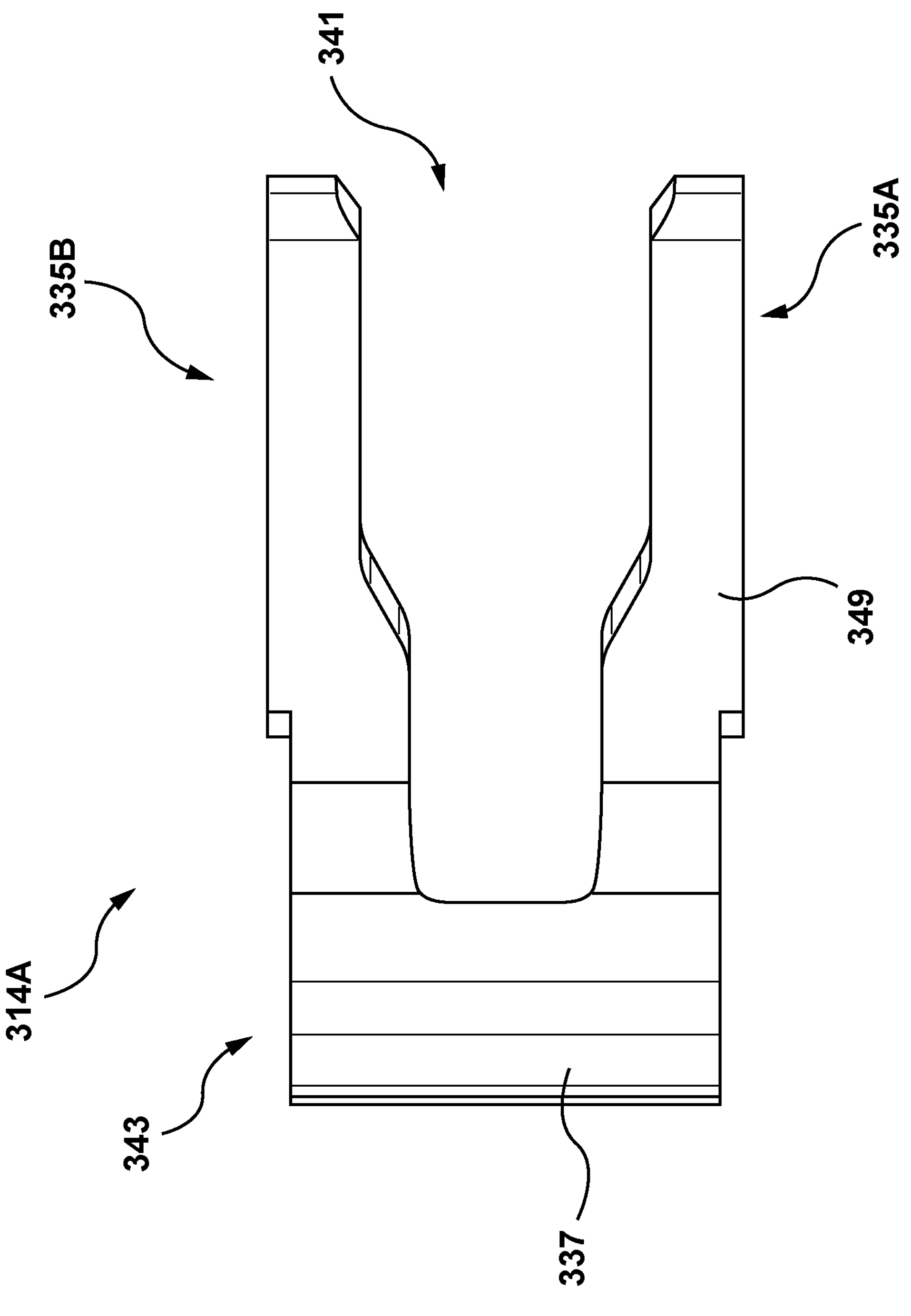
Figure 9D:
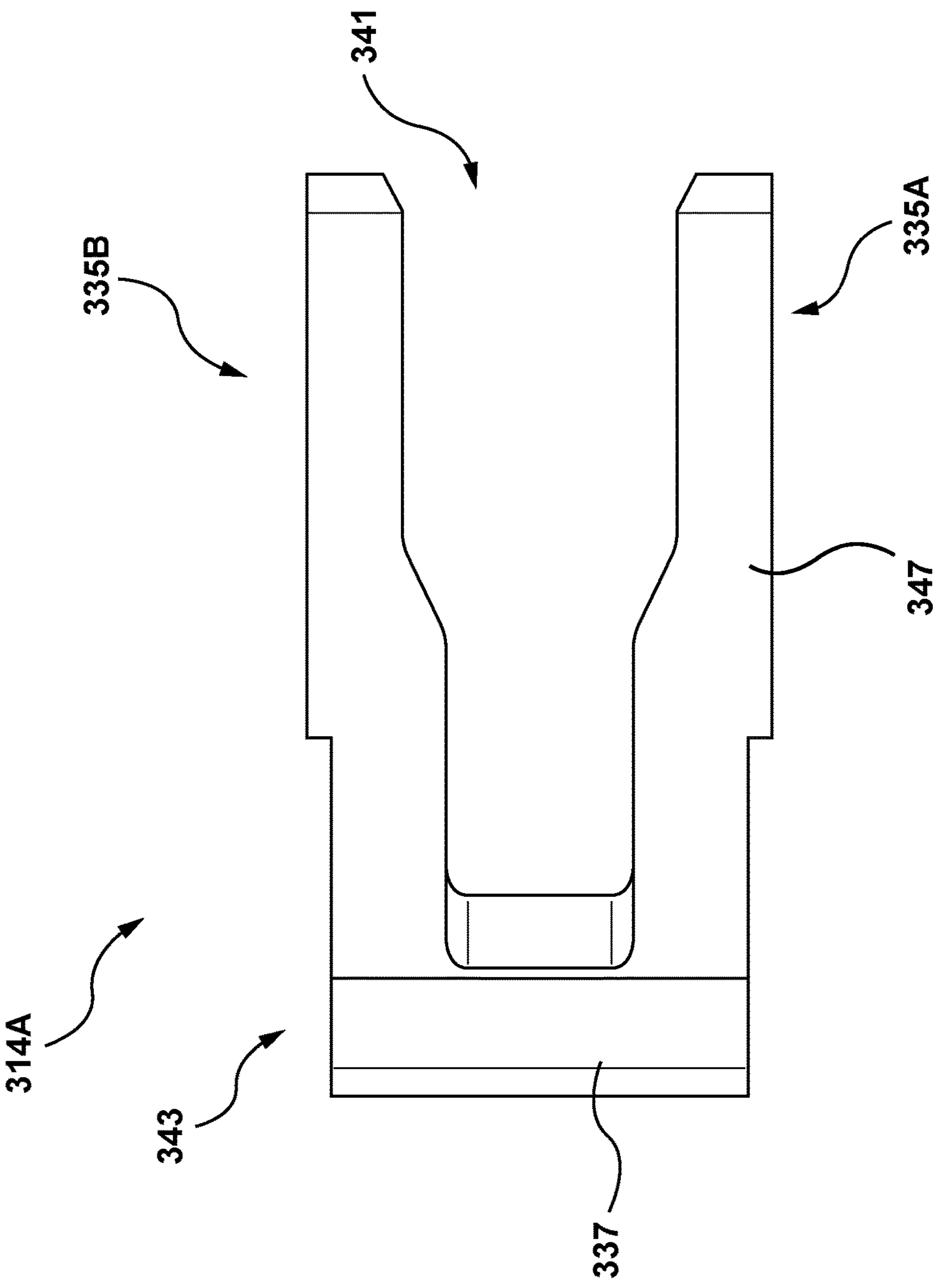

FIGS. 8A and 8B depict perspective and front views, respectively, of a rod 318. While only one rod 318 is discussed, one skilled in the art will realize that all of the rods 318 of the crimper 200 have the same configuration and include the same components as the rod 318 described in FIGS. 8A-8B.

A rod 318 is disposed within each rod channel 311, and functions or operates to couple the cam 310 to the plurality of crimper elements 314. Each rod of the plurality of rods 318 extends from the cam 310 to a middle region of one of the crimper elements 314. The rods 318 are rotatably coupled to the cam 310. That is, when the cam 310 rotates in response to movement of the handle 302, the rods 318 are allowed to rotate relative to the cam 310. Likewise, the rods 318 are rotatably coupled to the crimper elements 314. That is, when the rods 318 rotate in response to the rotation of the cam 310, the crimper elements 314 are allowed to move radially relative to the rods 318.

As illustrated, the rod 318 includes a base 319 and two parallel legs 325 extending from the base 319. The legs 325 of the rod 318 each include a connection hole 329. After assembly, the connection holes 329 align with the connection hole 327 of the cam 310, described above. The connection holes 329 are similarly sized and shaped to connection holes 315 of the cam 310, and are configured to receive a pin (not shown) that couples the cam 310 to a rod 318. Stated another way, a plurality of pins are utilized to couple the cam 310 to the rods 318, with each pin passing through the connection hole 315 of the cam 310 and passing through connection holes 329 of the rods 318. For example, the pin can be a dowel pin, a bolt, and the like. The pin can be formed to a diameter to maintain the corresponding circular openings and cause the pin to operate as a fulcrum. When the cam 310 rotates clockwise or counter-clockwise, the combination of the pin and the connection holes 329 allow the rod 318 to rotate about the pin, with movement of the rod 318 being limited by the rod channel 311 of the cam 310. Thus, the rod channels 311 of the cam 310 are configured to provide clearance and permit rotational movement of the of the rods 318 relative to the cam 310. When assembled to the cam 310, the cam 310 is disposed within the space between the legs 325 of the rod 318 and the connection holes 329 of the legs 325 are aligned with the connection hole 315 of the cam 310.

The base 319 of each rod 218 may include a rounded end 327A that is formed in a semi-cylindrical shape. The rounded end 327A includes a connection hole 327 formed or extending therethrough. Each connection hole 327 is configured to receive a pin (not shown) that couples the rod 318 to a crimper element 314. Stated another way, a plurality of pins are utilized to couple the rod 318 to the crimper element 314, with each pin passing through the connection hole 327 and passing through a similar connection hole formed through the crimper element 314. For example, the pin can be a dowel pin, a bolt, and the like. After assembly, the connection hole 327 aligns with the connection holes of the crimper element 314 and the aligned connection holes and a pin disposed therethrough operate to moveably couple a crimper element 314 to a rod 318.

Each rod 318 is a relatively rigid element with minimal or no bend and/or deformation during operation of the crimper 200. Because each rod 318 is fixed at one end to the cam 310 and at the opposite end to one of the crimper elements 314, when the cam 310 is rotated, the distance between the connection of the rod 318 to the cam 310 and the connection of the rod 318 to the crimper element 314 must remain the same. However, as the cam 310 is rotated, that distance can only remain the same if the crimper element 314 is pushed radially inward by the rods 318. Thus, rotation of the cam 310 forces the crimper elements 314 inward via the rods 318. In particular, the crimper elements 314 move radially inward generally towards the center of the crimper chamber 216.

FIGS. 9A-9D depict different views of a crimper element 314 of the crimper 200. The plurality of crimper elements 314 may be considered to include a first plurality of crimper elements 314A and a second plurality of crimper elements 314B. The structure of the crimper elements 314A and the structure of the crimper elements 314B are the same, except that each crimper element 314B include an integral channel formed therethrough, as will be described in more detail with respect to FIG. 10, such that each crimper element 314B is configured to receive and deliver fluid from the fluid source 264 and a respective tubing component 266. FIGS. 9A-9D depict different views of a crimper element 314A. While only one crimper element 314A is discussed, one skilled in the art will realize that all of the crimper elements 314A, 314B of the crimper 200 have the same configuration and include the same components as the crimper element 314A described in FIGS. 9A-9D, except for the differences described herein.

In operation, the crimper elements 314 are displaced by the movement of the handle 302. That is, as the handle 302 is moved, the cam 310 rotates and functions to translate or transform the rotational motion of the handle 302 into linear motion of the crimper elements 314 via the rods 318. As such, the crimper elements 314 function as an iris to decrease or increase the volume of the crimper chamber 216 through the movement of the handle 302.

Each crimper element 314 has a first leg 335A, a second leg 335B, and a crimper lobe 337 coupled to and extending between the first leg 335A and the second leg 335B. The first leg 335A and the second leg 335B extend parallel to a long axis of the crimper element 314, from a first end 339 of the crimper element 314 to the crimper lobe 337. The first leg 335A and the second leg 335B are spaced apart and define a rod channel 341 therebetween. A connection hole 331 is formed in each of the first leg 335A and the second leg 335B such that the crimper element 314 includes a total of two connection holes. In embodiments, the connection holes 331 can be configured to receive a pin that passes through the two connection holes 331 and the connection hole 327 of the rod 318. For example, the pin can be a dowel pin, a bolt, and the like. The pin can be formed to a diameter to maintain the corresponding circular openings and cause the pin to operate as a fulcrum. The connection holes 331 operate to moveably couple the crimper elements 314 to the rod 318. The rods 318 are disposed between the legs 335A, 335B of the crimper element 314, within the rod channel 341 of the crimper element 314 and with the connection hole 327 of the rod 318 aligned with the connection holes 331 of the crimper element 314. The rod channel 341 is sized to permit the rods 318 to rotate relative to the crimper elements 314 during operation of the crimper 200.

The crimper lobe 337 extends from the first leg 335A and the second leg 335B to a second end 343 of the crimper element 314. The crimper lobe 337 defines a crimper space 345, or stated another way, includes the crimper space 345 defined therein. The crimper space 345 is configured to accommodate or receive an adjacent or neighboring crimper element 314 when the crimper 200 is operated and the crimper chamber 216 decreases in size or volume. More particularly, the crimper element 314 includes a first side or exterior surface 347 and a second side or interior surface 349 formed on the opposing side thereof. When assembled into the crimper 200, the exterior surface 347 of a crimper element 314 is disposed adjacent to the interior surface 349 of a neighboring crimper element such that the crimper element 314 is received into the crimper space 345 of the neighboring crimper element.

Along the exterior surface 347 of the crimper lobe 337, the crimper lobe 337 includes a first exterior ramp 357A and a second exterior ramp 357B. The first exterior ramp 357A and the second exterior ramp 357B are angled surfaces relative to a long axis of the crimper element 314. Along the interior surface 349 of the crimper lobe 337, the crimper lobe 337 includes a first interior ramp 359A and a second interior ramp 359B. The first interior ramp 359A and the second interior ramp 359B define the crimper space 345, and thus are configured to contact a neighboring crimper element to generate the iris effect when the crimper elements are displaced. The first interior ramp 359A and the second interior ramp 359B can be formed at angles relative to a long axis of the crimper element 314.

The dimensions of the crimper element 314 can be governed by a size of the object being crimped. In an embodiment, the axial length of the crimper chamber 216 can range from approximately 20 mm to approximately 50 mm and the diameter thereof can range from approximately 1 mm to approximately 40 mm. In an embodiment, the angle formed between the second exterior ramp 357B and the first interior ramp 359A depends on the crimper elements included in the crimper 200. More particularly, the angle formed between the second exterior ramp 357B and the first interior ramp 359A may be determined by dividing 360 degrees by the number of crimper elements 314 in the crimper 200. In an embodiment, the number of crimper elements can range from 8 to 16. In another embodiment, the number of crimper elements can range from 10 to 12. The angle or slope of each of the first exterior ramp 357A and the second interior ramp 359B are set or configured to allow the crimper elements 314 to clear each other during operation of the crimper 200.

Figure 10:
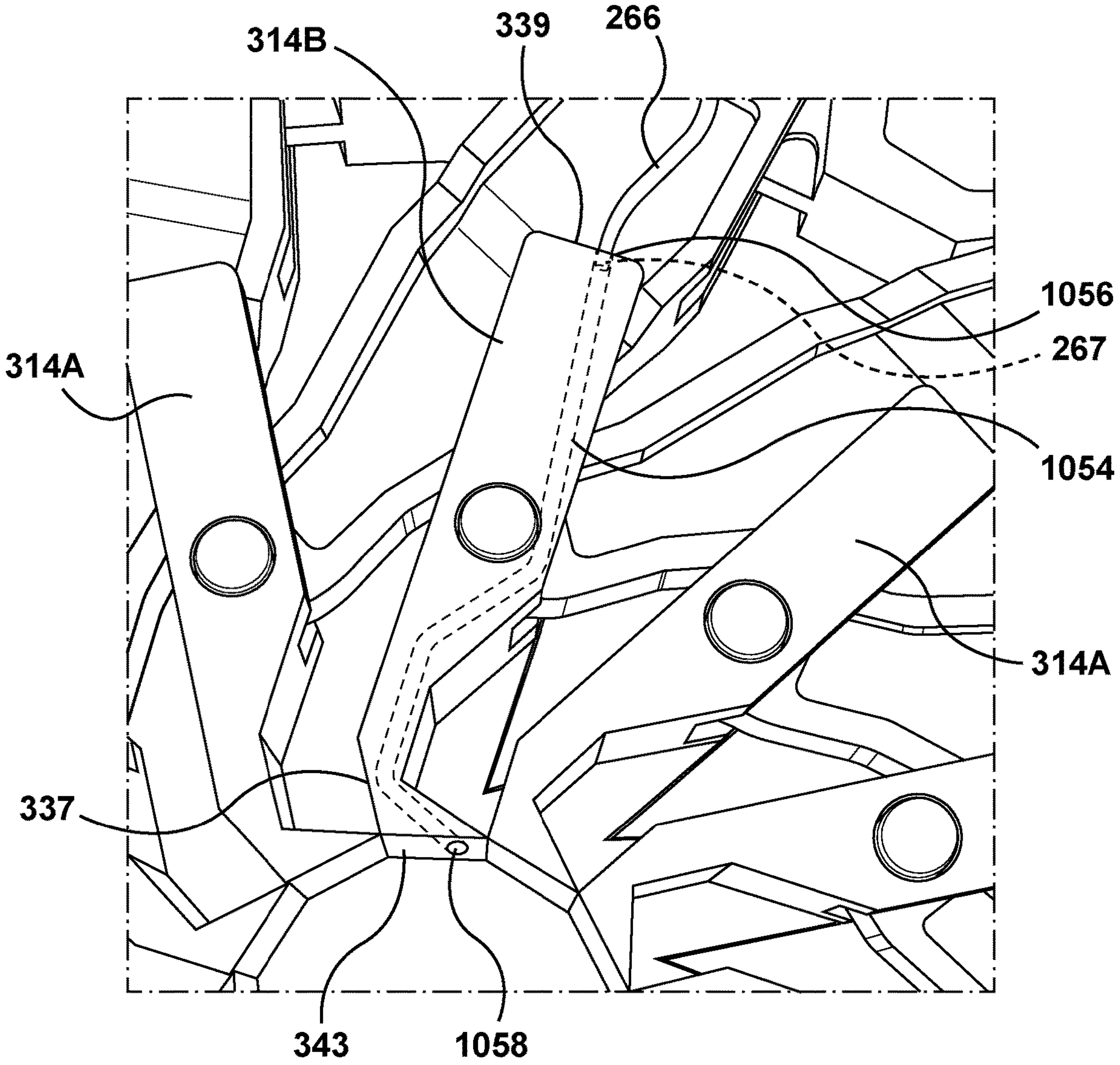
FIG. 10 is a perspective view of a portion of the crimper of FIGS. 3 and 4, illustrating a connection between tubing component and a crimper element of the crimper.

As described above, since the transcatheter valve prosthesis 170 includes exactly three leaflets 176, the crimper 200 includes exactly three crimper elements 314B which are configured to receive and deliver fluid from a respective tubing component 266. The exactly three crimper elements 314B are equally and circumferentially spaced apart from each other, and are spaced to align with the three leaflets 176 of the transcatheter valve prosthesis 170. The structure of all of the crimper elements 314 is the same, except that each crimper element 314B further includes an integral channel formed therethrough to receive and deliver fluid from a respective tubing component 266. More particularly, as shown in FIG. 10, each crimper element 314B includes an integral channel 1054 having an inlet 1056 formed at or on the first end 339 of the crimper element and an outlet 1058 formed at or on the second end 343 of the crimper element. Stated another way, the integral channel 1054 extends through an entire length of the crimper element 314B. The inlet 1056 may be formed on either leg 335A, 335B of the crimper element 314B, while the outlet 1058 is formed on the crimper lobe 337 of the crimper element 314B. It will be apparent to one of ordinary skill in the art that the illustrated configuration or path of the integral channel 1054 through the crimper element 314B is exemplary only, and the integral channel 1054 may be formed with various different paths or configurations through the length of the crimper element 314B. An end 267 of the respective tubing component 266 is configured to be coupled to the crimper element 314B adjacent to the inlet 1056 of the integral channel 1054 such that the tubing component 266 is in fluid communication with the integral channel 1054, while the opposing end (not shown in FIG. 10) of the respective tubing component 266 is attached to the fluid source 264. In an embodiment, in order to be coupled to the integral channel 1054, the tubing component 266 may extend through a portion of or the full length of the integral channel 1054. The integral channel 1054 is thus sized or configured to receive the tubing component 266. The tubing component 266 may be placed into the integral channel 1054 by a user prior to use of the crimper 200. In another embodiment, in order to be coupled to the integral channel 1054, the end 267 of the tubing component 266 may be bonded, welded, or otherwise attached to the inlet 1056.

Pressurized fluid from the fluid source 264 is delivered through the tubing components 266 and through each crimper element 314B. When the pressurized fluid exits from each crimper element 314B via the outlet 1058, the pressurized fluid is directed in a radial direction onto the leaflets 176 of the transcatheter valve prosthesis 170 disposed within the crimper chamber 216 of the crimper 200. The leaflets 176 are thereby deflected or displaced radially inwards by the pressurized fluid during the crimping process. The fluid path of the integral channel 1054 may be configured to act normal or perpendicular to the crimper element 314B, or at an angle to apply more of a back pressure on the leaflet 176. More particularly, in the embodiment depicted in FIG. 10, the integral channel 1054 is formed such that the pressurized fluid exits from each crimper element 314B at a non-perpendicular angle relative to the second exterior ramp 357B of the crimper element 314B (which forms a portion of the crimper chamber 216). As the diameter of the crimper chamber 216 is reduced, the outlet 1058 may be obstructed or blocked by an overlapping crimper element 314. When the pressurized fluid exits from the crimper element 314B at an angle rather than normal or perpendicular, the pressurized fluid applies a backpressure on the leaflets 176 and ensures that there is an unobstructed fluid path for at least the start of the crimp procedure for each valve size. Stated another way, the outlet 1058 is not blocked through at least a partial crimp stage of the transcatheter valve prosthesis 170. However, it is not required that the pressurized fluid exits from the crimper element 314B at an angle rather than normal or perpendicular and thus in another embodiment hereof, the pressurized fluid may exit from the crimper element 314B at a normal or perpendicular angle relative to the second exterior ramp 357B of the crimper element 314B.

The crimper elements 314B may be formed by 3D printing to include the integral channel 1054. In another embodiment, the crimper elements 314B may be formed in two separate pieces and the integral channel 1054 may be machined into one or both pieces prior to assembly of the two pieces. The crimper elements 314B may be labeled, formed of a different color, or otherwise marked such that the user can clearly distinguish the crimper elements 314B from the crimper elements 314A. Distinguishing the crimper elements 314B from the crimper elements 314A allows a user to circumferentially align the transcatheter valve prosthesis 170 as desired with the crimper elements 314B prior to crimping such that each crimper element 314B (and corresponding fluid path) is aligned with a center of each leaflet 176.

Figure 11A:
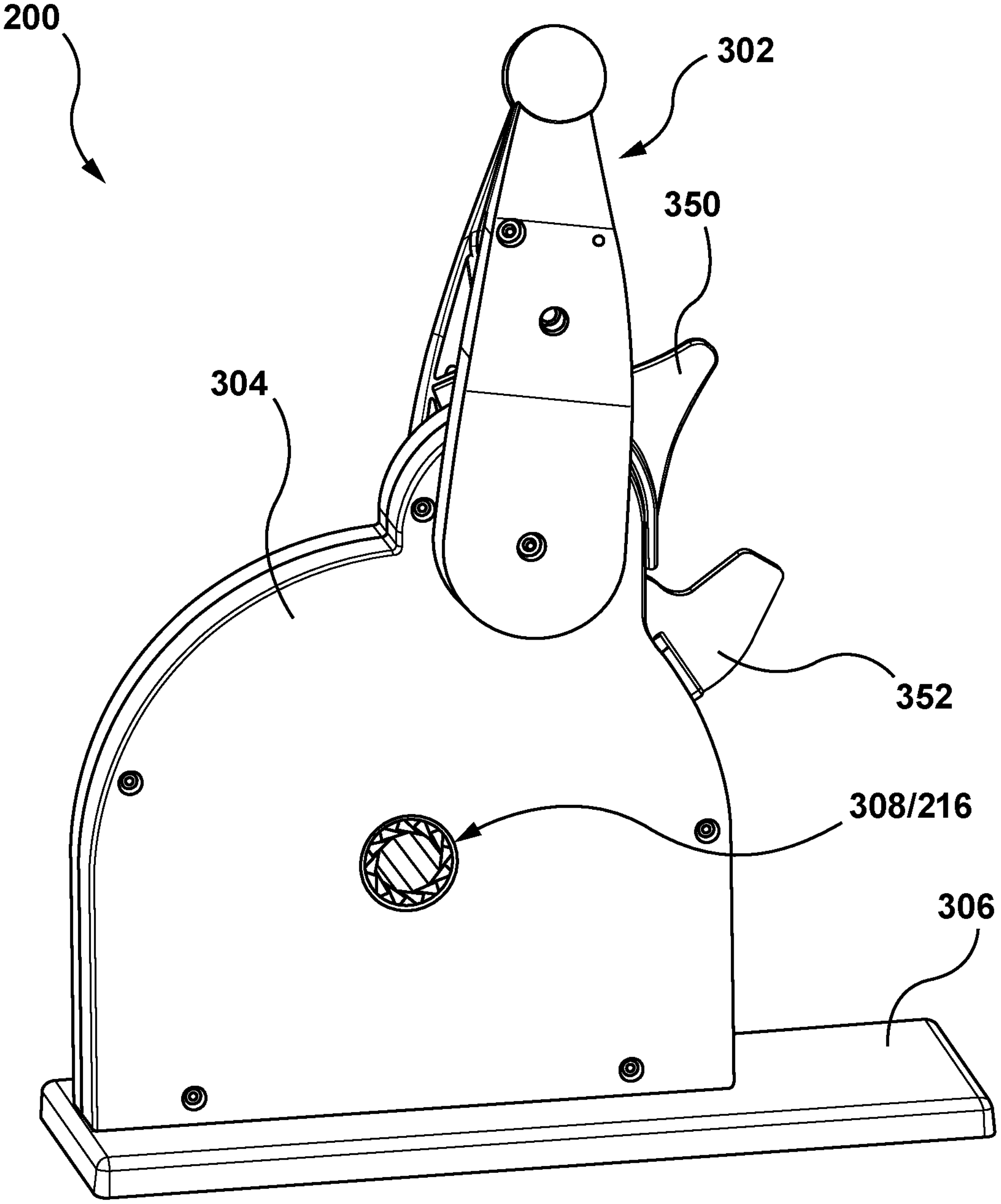
FIGS. 11A-11D depict an operation of the crimper of FIGS. 3 and 4.
Figure 11B:
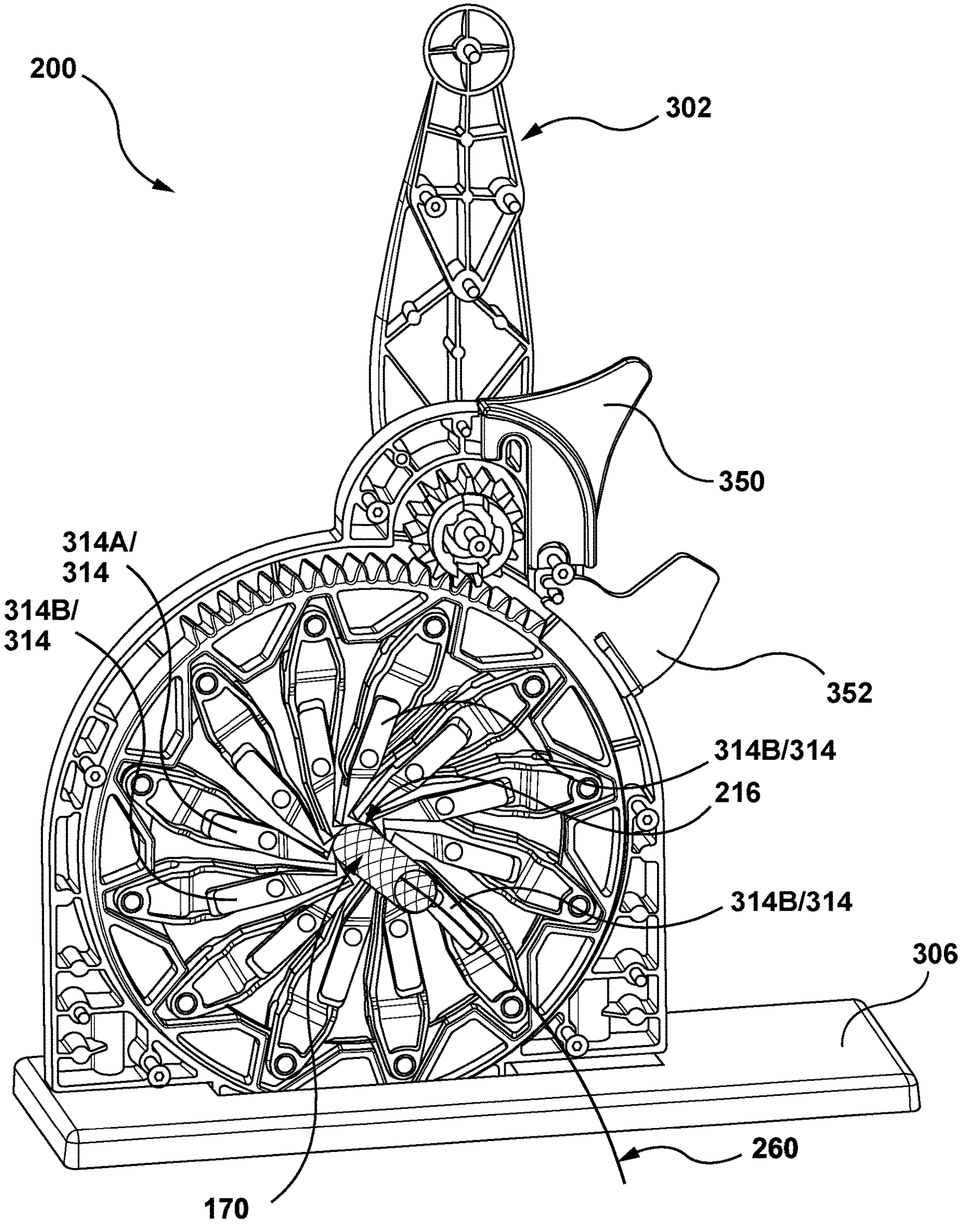
Figure 11C:
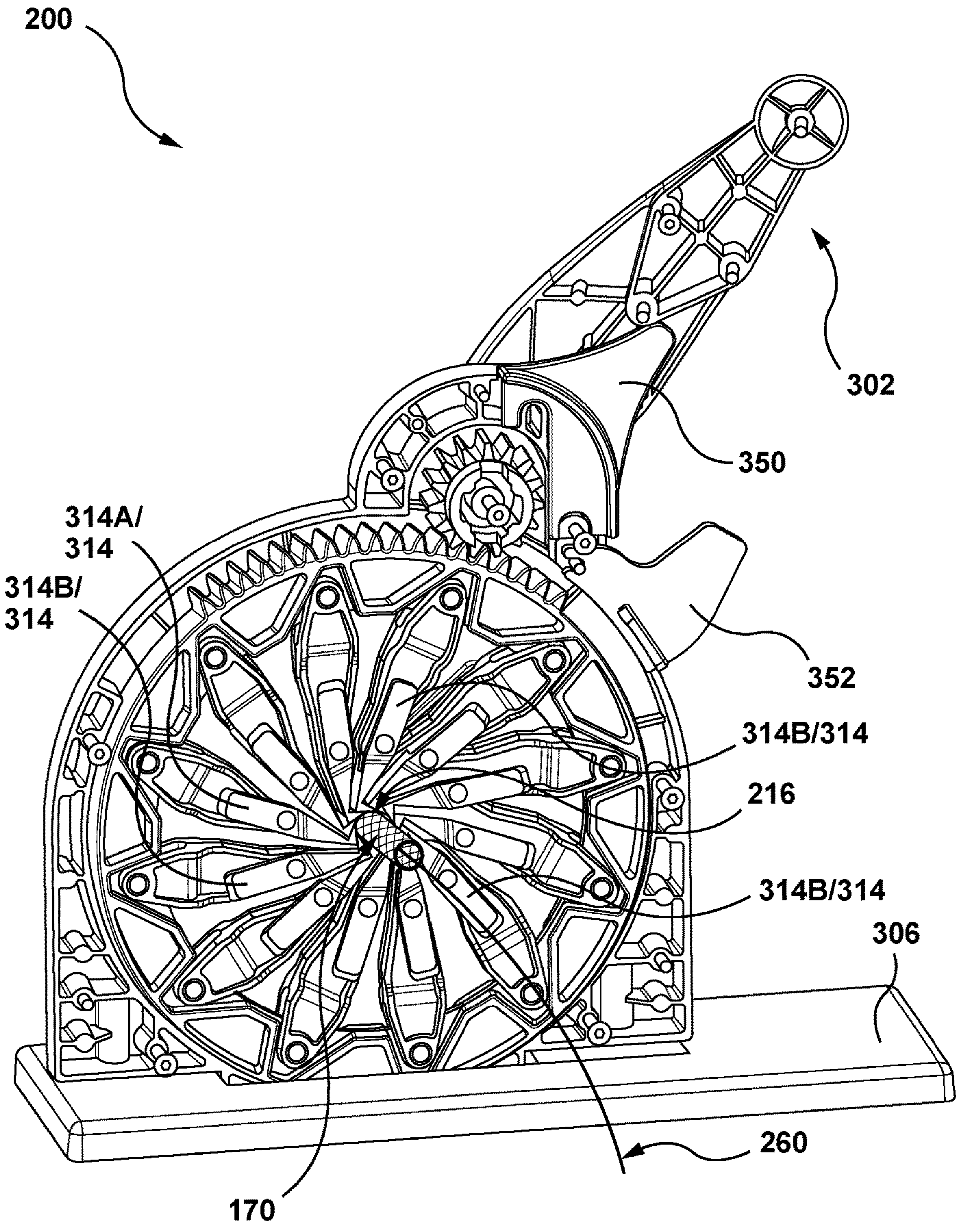
Figure 11D:
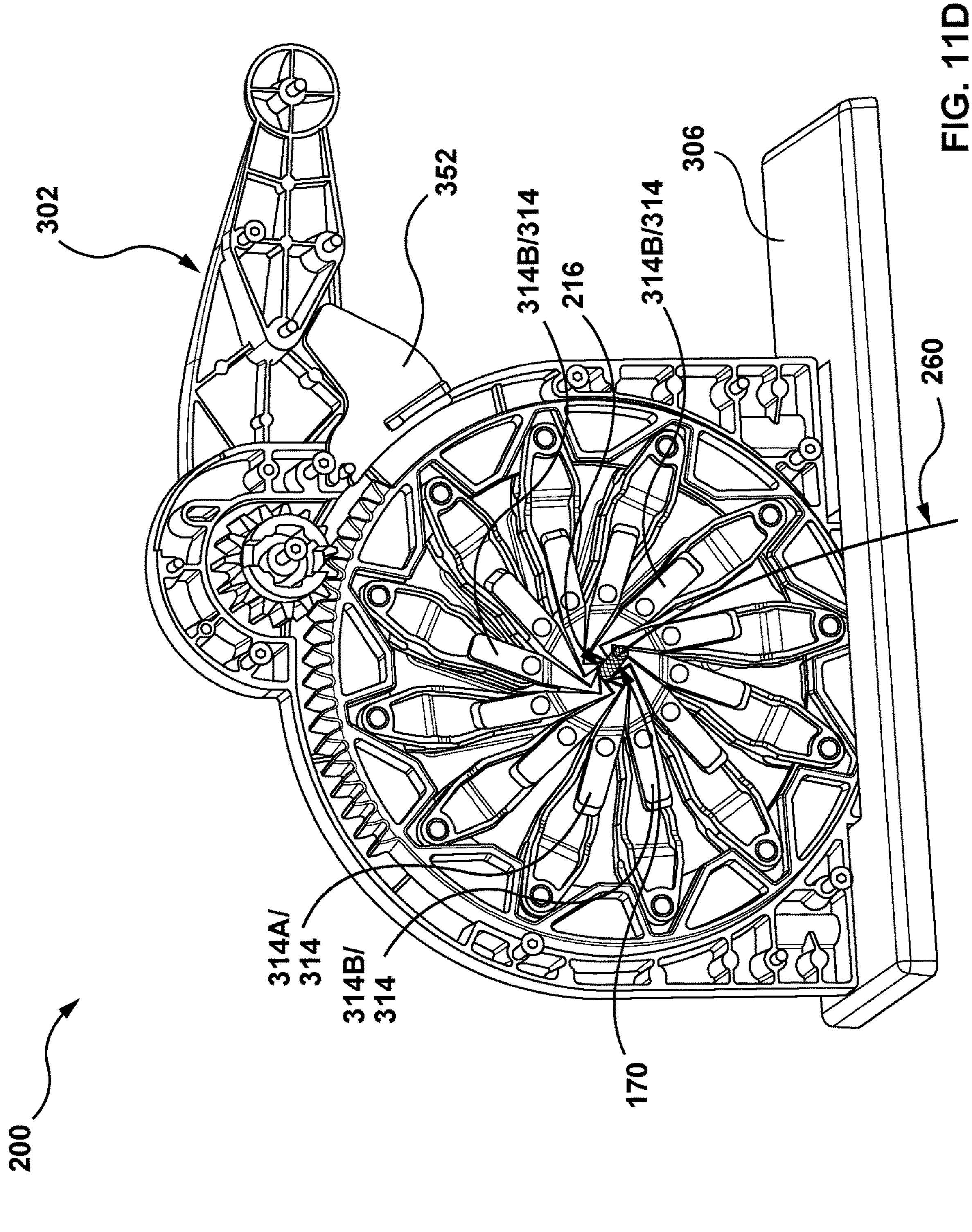
Figure 12:
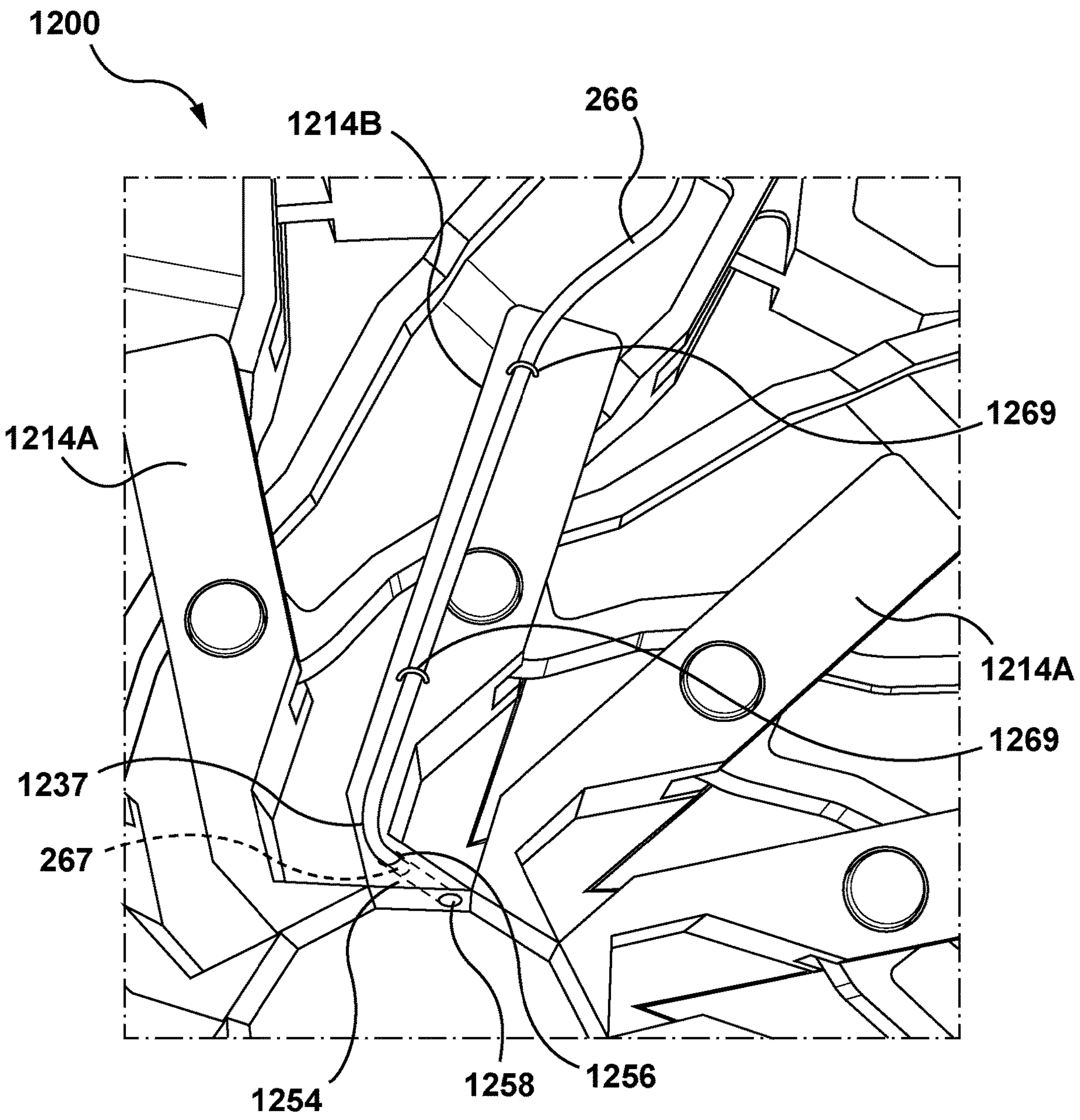
FIG. 12 is a perspective view of a portion of a crimper according to another embodiment hereof, illustrating a connection between tubing component and a crimper element of the crimper, wherein the tubing component is coupled to an exterior surface of the crimper element.

FIGS. 11A-11D illustrate the operation of the crimper 200 in accordance with an embodiment hereof. As illustrated in FIG. 11A and FIG. 11B, the transcatheter valve prosthesis 170 and the delivery device 260 is loaded or placed into the crimper chamber 216 of the crimper housing 304. As described above, the crimper elements 314 form the crimper chamber 216. As illustrated in FIG. 11C-11D, to compress the transcatheter valve prosthesis 170, a force is applied to the handle 302 in the direction of the base 306 in a clockwise direction. The force applied to the handle 302 is transferred to the cam 310 via the gear 312, and the cam 310 rotates in an opposing direction from the handle 302, i.e., a counterclockwise direction. Rotation of the cam 310 causes the crimper elements 312 to move radially inward via the rods 318. More particularly, as described above, as the handle 302 moves, the cam 310 rotates and translates or transforms the rotational motion of the handle 302 into linear motion of the crimper elements 314 via the rods 318.

As the crimper elements 314 move radially inward, the space available for the crimper elements 314 to occupy is reduced. As such, the volume of the crimper chamber 216 decreases and the crimper elements 314 apply a compression force to external surfaces of the transcatheter valve prosthesis 170 to crimp the transcatheter valve prosthesis 170 from an uncompressed or radially expanded state to a radially compressed state. For example, if the transcatheter valve prosthesis 170 is generally cylindrical in shape, the crimper elements apply a force on the surface of the transcatheter valve prosthesis from various directions as force is applied to the handle 302 thereby compressing the implantable medical device. During the crimping process, pressurized fluid is delivered from the fluid source 264 to the leaflets 176 of the transcatheter valve prosthesis 170 to urge the leaflets 176 radially inwards. The fluid is applied radially to an exterior surface of the leaflets 176 of the transcatheter valve prosthesis 170 such that the fluid pushes the leaflets 176 radially inwards. Displacing the leaflets 176 radially inwards during the crimping process minimizes the risk of leaflet protrusion and damage.

As illustrated in FIG. 11C, the handle 302 can be moved downward until the handle 302 abuts the first stop 350, thereby partially compressing the transcatheter valve prosthesis 170 to a predetermined diameter. If the transcatheter valve prosthesis 170 requires only a partial compression, the handle 302 can be moved upward and the transcatheter valve prosthesis 170 removed from the crimper chamber 216.

If the transcatheter valve prosthesis 170 is to be fully compressed, the first stop 350 is removed from the crimper 304 and the handle 302 is further actuated or moved until the handle 302 abuts the second stop 352 as illustrated in FIG. 11D. The further movement of the handle 302 causes additional radial compression of the transcatheter valve prosthesis 170.

The crimper 200 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices.

FIG. 12 is a perspective view of a portion of a crimper 1200 according to another embodiment hereof. The crimper 1200 is the same as crimper 200 except for the differences explained below. More particularly, the crimper 1200 includes exactly three crimper elements 1214B which are configured to receive and deliver fluid from a respective tubing component 266. The crimper elements 1214B are the same as the crimper elements 314B, except that the integral channel for fluid delivery is not formed through the entire length of the crimper element. Rather, in the embodiment of FIG. 12, a relatively shorter integral channel 1254 is formed only within the crimper lobe 1237 of the crimper element 1214B. The relatively shorter integral channel 1254 may be drilled or machined into the crimper element 1214B, and thus may be easier to form compared to the integral channels 1054 which extend the full length of the crimper element 314B.

More particularly, as shown in FIG. 12, the integral channel 1254 has an inlet 1256 and an outlet 1258. Both of the inlet 1256 and the outlet 1258 are formed on the crimper lobe 1237 of the crimper element 1214B. The end 267 of the respective tubing component 266 is configured to be coupled to the crimper element 1214B adjacent to the inlet 1256 of the integral channel 1254 such that the tubing component 266 is in fluid communication with the integral channel 1254, while the opposing end (not shown in FIG. 12) of the respective tubing component 266 is attached to the fluid source 264. The end 267 of the tubing component 266 may be bonded, welded, or otherwise attached to the inlet 1256, or in another embodiment, the tubing component 266 may extend through a portion of or the full length of the integral channel 1254. In this embodiment, the tubing component 266 extends alongside or adjacent to the exterior of the crimper element 1214B as shown in FIG. 12 and may be held in place via one or more loops 1269. The loops 1269 are attached to the exterior of the crimper element 1214B and are configured to receive the tubing component 266 therethrough, such that the tubing component 266 is secured to the crimper element 1214B and does not move relative thereto during the crimping process.

Pressurized fluid from the fluid source 264 is delivered through the tubing components 266 and through each crimper element 1214B. When the pressurized fluid exits from each crimper element 1214B via the outlet 1258, the pressurized fluid is directed in a radial direction onto the leaflets 176 of the transcatheter valve prosthesis 170 disposed within the crimper chamber 216 of the crimper 200. The leaflets 176 are thereby deflected radially inwards by the pressurized fluid during the crimping process. Similar to the integral channel 1054, the fluid path of the integral channel 1254 may be configured to act normal or perpendicular to the crimper element 1214B, or at an angle to apply more of a back pressure on the leaflet 176.

Figure 13:
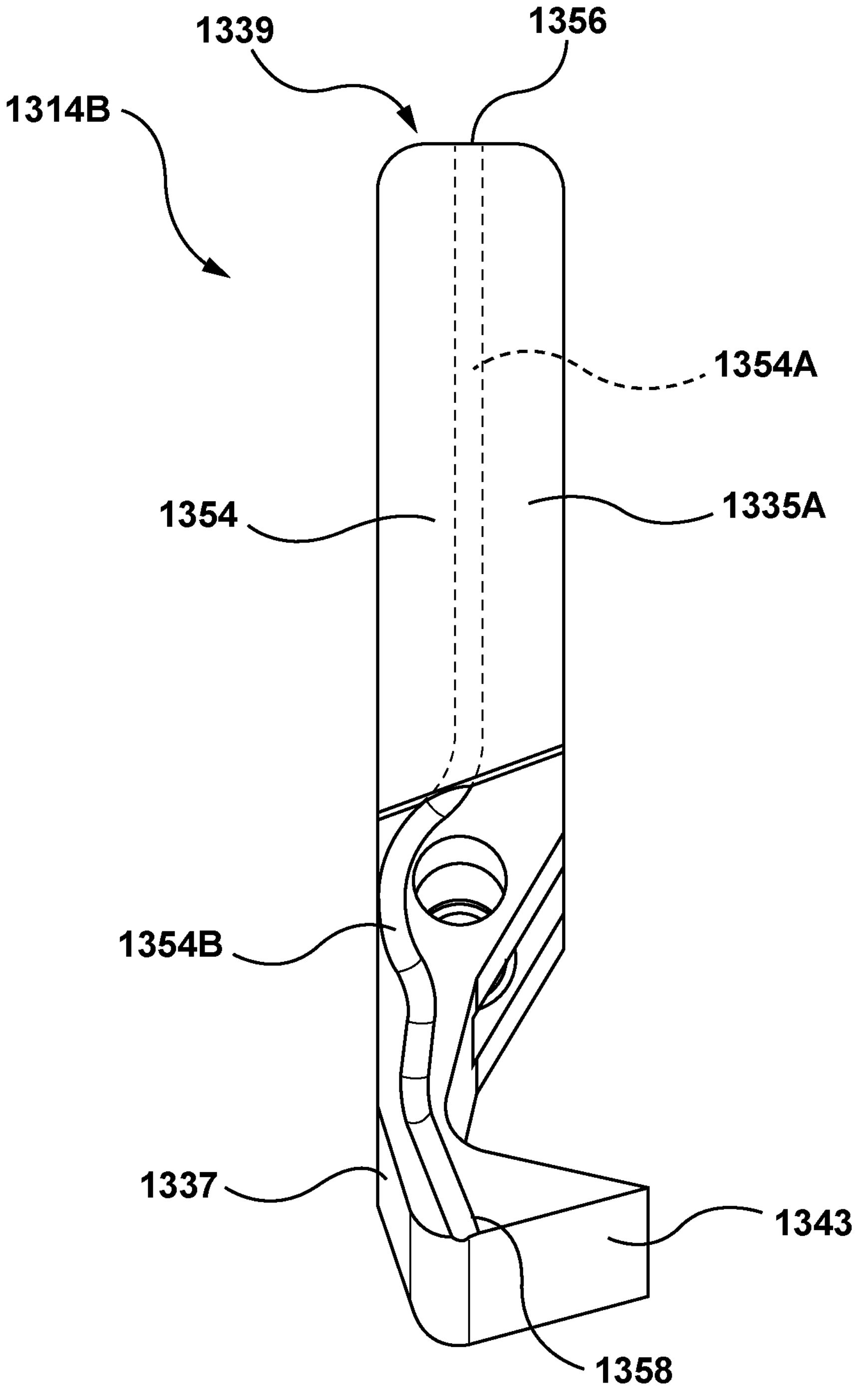
FIG. 13 is a perspective view of a crimper element according to another embodiment hereof.

FIG. 13 is a perspective view of a portion of a crimper element 1314B according to another embodiment hereof. The crimper element 1314B is an alternative embodiment of the crimper element 314B. The crimper element 1314B is the same as the crimper elements 314B, except that the integral channel for fluid delivery is not formed through the entire length of the crimper element. Rather, in the embodiment of FIG. 13, an integral channel 1354 includes a first portion 1354A which is formed within a crimper leg 1335A of the crimper element 1314B and a second portion 1354B which is formed on an outer surface of a crimper lobe 1337 of the crimper element 1314B. The first portion 1354A of the integral channel 1354 may have a generally circular cross-section, while the second portion 1354B is a groove that may have a generally semi-circular cross-section.

More particularly, as shown in FIG. 13, the integral channel 1354 has an inlet 1356 and an outlet 1358. The integral channel 1354 has an inlet 1356 formed at or on a first end 1339 of the crimper element 1314B and an outlet 1358 formed at or on the second end 1343 of the crimper element 1314B. Stated another way, the integral channel 1354 extends through an entire length of the crimper element 1314B. The inlet 1356 may be formed on either leg of the crimper element 1314B, while the outlet 1358 is formed on the crimper lobe 1337 of the crimper element 1314B. The tubing component 266 (not shown on FIG. 13) may extend through the full length of the integral channel 1354. More particularly, the tubing component 266 is configured to extend through the first portion 1354A of the integral channel 1354 and is configured to sit within the second portion 1354B of the crimper element 1314B.

Pressurized fluid from the fluid source 264 is delivered through the tubing components 266 and through each crimper element 1314B. When the pressurized fluid exits from each crimper element 1314B via the outlet 1358, the pressurized fluid is directed in a radial direction onto the leaflets 176 of the transcatheter valve prosthesis 170 disposed within the crimper chamber 216 of the crimper 200. The leaflets 176 are thereby deflected radially inwards by the pressurized fluid during the crimping process. Similar to the integral channel 1054, the fluid path of the integral channel 1354 may be configured to act normal or perpendicular to the crimper element 1314B, or at an angle to apply more of a back pressure on the leaflet 176.

Figure 15:
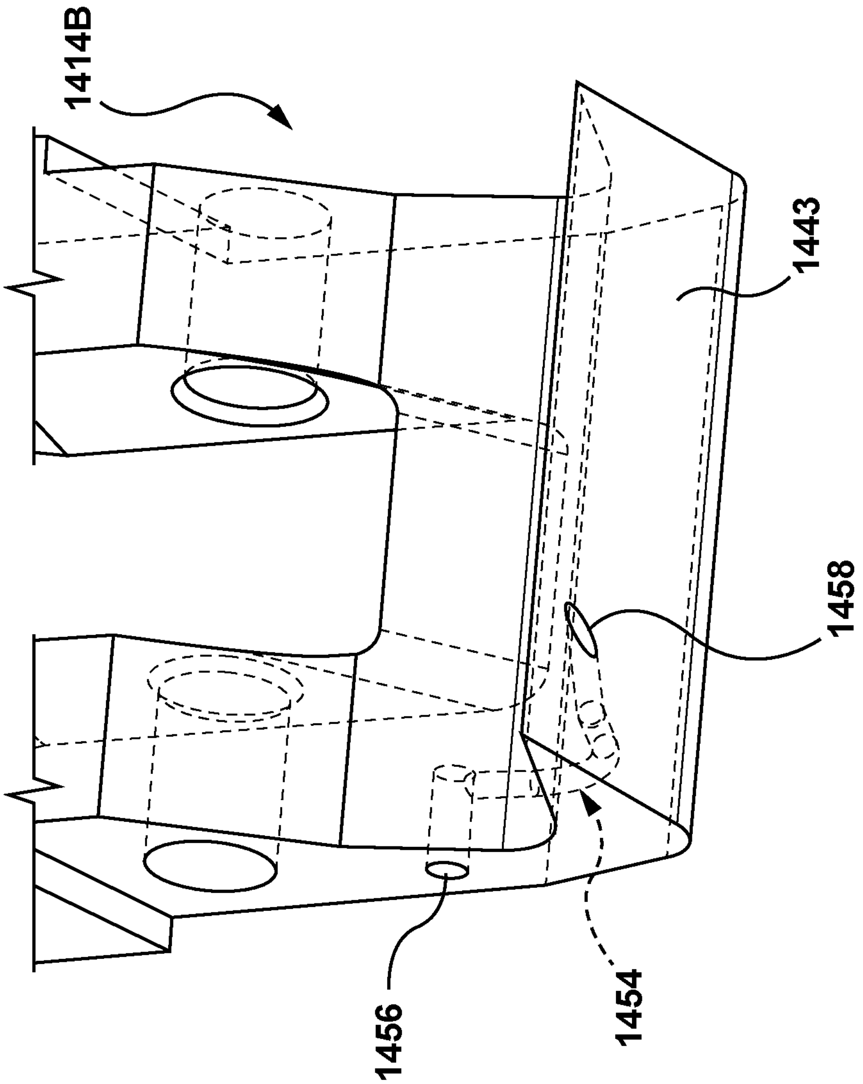
FIG. 15 is a perspective view of a portion of the crimper element of FIG. 14.
Figure 14:
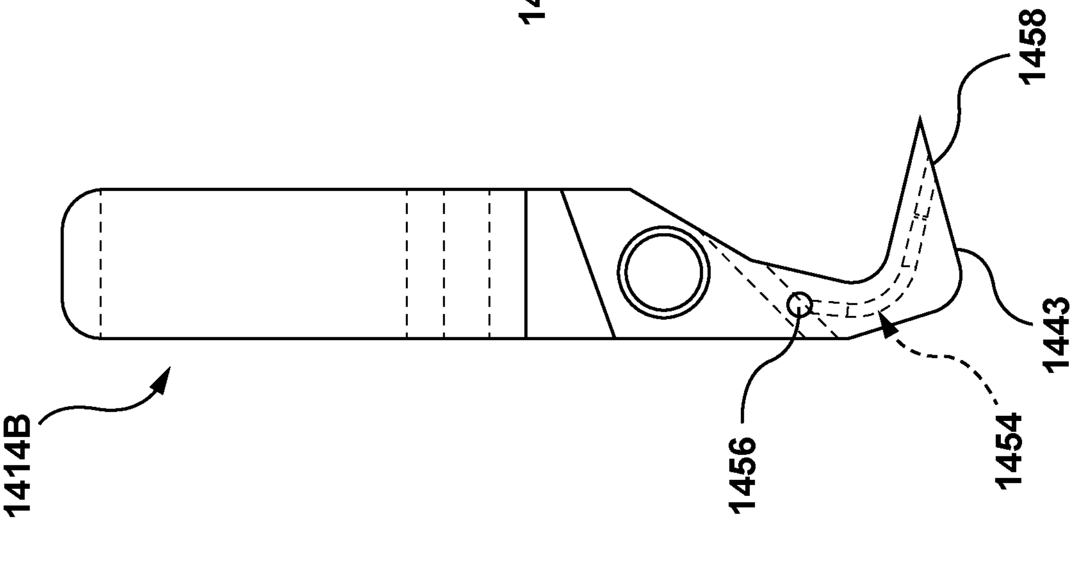
FIG. 14 is a side view of a crimper element according to another embodiment hereof.

Although embodiments hereof depict the tubing components 266 being coupled to a top end of the crimper 200 (with the top end being defined as the end opposite from the base 306), it will be apparent to one of ordinary skill in the art that the tubing components 266 may alternatively enter into the crimper 200 at other locations. In an embodiment, for example, the tubing components 266 may enter into the crimper 200 through a front of the crimper 200, at the opening 308. At least a portion of the crimper elements 314A, 314B are accessible to the user through the opening 308. The inlet 356 of the integral channel 354 described herein may be modified such that it is disposed on the crimper element 314B so to be accessible to the user through the opening 308, and the tubing component 266 may be coupled to the inlet 356 through the opening 308. For example, FIGS. 14 and 15 depict a crimper element 1414B configured to couple to the tubing components 266 through the opening 308. FIG. 14 is a side view of the crimper element 1414B, and FIG. 15 is a perspective view of a portion of the crimper element 1414B. The crimper element 1414B is an alternative embodiment of the crimper element 314B. The crimper element 1414B is the same as the crimper elements 314B, except for the configuration of the integral channel for fluid delivery. In the embodiment of FIG. 15, an integral channel 1454 has an inlet 1456 and an outlet 1458. The inlet 1456 is formed at or on the crimper element 1414B so to be accessible to the user through the opening 308 of the crimper 200 and an outlet 1458 is formed at or on a second end 1443 of the crimper element 1414B. The tubing component 266 (not shown on FIGS. 14 and 15) may be coupled to the inlet 1456 through the opening 308 of the crimper 200. Pressurized fluid from the fluid source 264 is delivered through the tubing components 266 and through each crimper element 1414B. When the pressurized fluid exits from each crimper element 1414B via the outlet 1458, the pressurized fluid is directed in a radial direction onto the leaflets 176 of the transcatheter valve prosthesis 170 disposed within the crimper chamber 216 of the crimper 200. The leaflets 176 are thereby deflected radially inwards by the pressurized fluid during the crimping process. Similar to the integral channel 1054, the fluid path of the integral channel 1454 may be configured to act normal or perpendicular to the crimper element 1414B, or at an angle to apply more of a back pressure on the leaflet 176.

Figure 16:
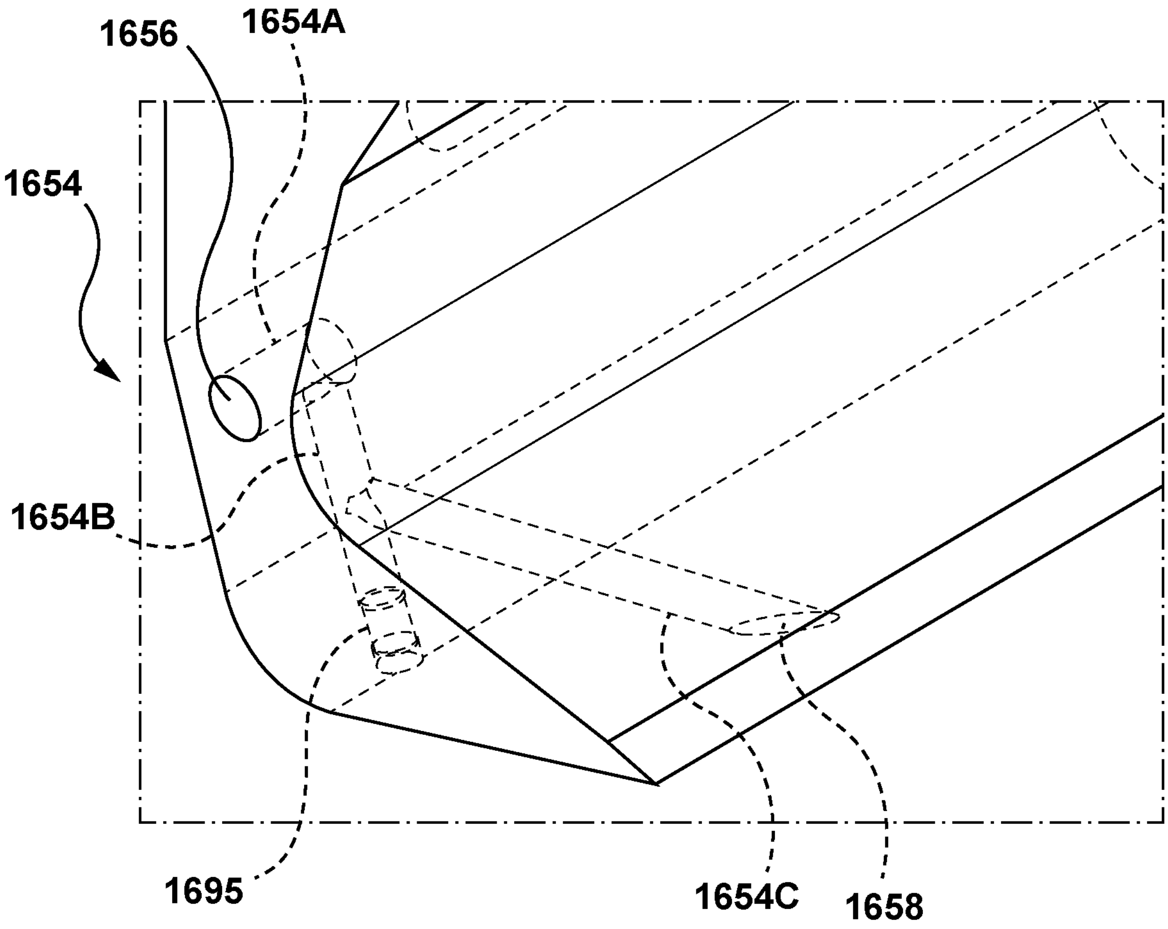
FIG. 16 is a perspective view of an integral channel according to another embodiment hereof, wherein the integral channel is formed via a plurality of drilled or machined holes.

Similar to the crimper elements 314B, the crimper elements 1414B may be formed by 3D printing to include the integral channel 1454 or may be formed in two separate pieces and the integral channel 1454 may be machined into one or both pieces prior to assembly of the two pieces. In another embodiment, which is depicted in FIG. 16, an integral channel 1654 takes a similar path as the integral channel 1454 but is formed via drilling or machining a plurality of holes or channels. The integral channel 1664 is formed using three drilled or machined channels 1654A, 1654B, 1654C that are in fluid communication with each other. A plug 1695 is disposed within the inlet of the second drilled channel 1654B so that the integral channel 1454 includes a single inlet 1656 (formed via the first drilled channel 1654A) and a single outlet 1658 (formed via the third drilled channel 1654C).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An assembly comprising:

a transcatheter valve prosthesis including a frame and a valve component including at least one leaflet disposed within and secured to the frame, the transcatheter valve prosthesis having a crimped configuration for delivery within a vasculature and an expanded configuration for deployment within a native heart valve; and a crimper for radially compressing the transcatheter valve prosthesis into the crimped configuration, the crimper being configured to apply pressurized fluid in a radial direction to the at least one leaflet of the transcatheter valve prosthesis to displace the at least one leaflet radially inwards when the crimper is radially compressing the transcatheter valve prosthesis.

2. The assembly of claim 1, wherein the crimper includes a plurality of crimper elements that collectively define a crimper chamber of the crimper, and wherein at least one crimper element of the plurality of crimper elements includes an integral channel extending therethrough for applying the pressurized fluid to the at least one leaflet.

3. The assembly of claim 2, wherein the integral channel extends from an inlet to an outlet, the inlet being formed at a first end of the at least one crimper element and the outlet being formed at a second end of the at least one crimper element, the second end opposing the first end.

4. The assembly of claim 2, wherein the at least one crimper element includes a first end and a second end, the second end opposing the first end, and wherein the integral channel extends from an inlet to an outlet, each of the inlet and the outlet being formed closer to the second end than the first end of the at least one crimper element.

5. The assembly of claim 4, further comprising one or more loops attached to an exterior surface of the least one crimper element, the one or more loops being configured to receive a tubing component therethrough.

6. The assembly of claim 2, wherein the at least one crimper element includes a first end and a second end, the second end opposing the first end and the second end including an exterior surface that defines a portion of the crimper chamber of the crimper, wherein a fluid path defined by the integral channel exits from the at least one crimper element at a non-perpendicular angle relative to the exterior surface of the second end.

7. The assembly of claim 2, wherein the transcatheter valve prosthesis includes exactly three leaflets and the crimper includes exactly three crimper elements that each include an integral channel extending therethrough for applying the pressurized fluid.

8. A crimper for radially compressing a transcatheter valve prosthesis having at least one leaflet into a crimped configuration, the crimper comprising:

a plurality of crimper elements that collectively define a crimper chamber of the crimper, wherein at least one crimper element of the plurality of crimper elements includes an integral channel extending therethrough for applying pressurized fluid in a radial direction to the at least one leaflet of the transcatheter valve prosthesis to displace the at least one leaflet radially inwards when the crimper is radially compressing the transcatheter valve prosthesis.

9. The crimper of claim 8, wherein the integral channel extends from an inlet to an outlet, the inlet being formed at a first end of the at least one crimper element and the outlet being formed at a second end of the at least one crimper element, the second end opposing the first end.

10. The crimper of claim 8, wherein the at least one crimper element includes a first end and a second end, the second end opposing the first end, and wherein the integral channel extends from an inlet to an outlet, each of the inlet and the outlet being formed closer to the second end than the first end of the at least one crimper element.

11. The crimper of claim 10, further comprising one or more loops attached to an exterior surface of the least one crimper element, the one or more loops being configured to receive a tubing component therethrough.

12. The crimper of claim 8, wherein the at least one crimper element includes a first end and a second end, the second end opposing the first end and the second end including an exterior surface that defines a portion of the crimper chamber of the crimper, wherein a fluid path defined by the integral channel exits from the at least one crimper element at a non-perpendicular angle relative to the exterior surface of the second end.

13. The crimper of claim 8, wherein the transcatheter valve prosthesis includes exactly three leaflets and the crimper includes exactly three crimper elements that each include an integral channel extending therethrough for applying the pressurized fluid.

14. A method of crimping a transcatheter valve prosthesis onto a delivery system, comprising:

positioning a transcatheter valve prosthesis into a crimper chamber of a crimper, the transcatheter valve prosthesis including a frame and a valve component including at least one leaflet disposed within and secured to the frame, wherein the transcatheter valve prosthesis is in an expanded configuration;

operating the crimper to radially compress the transcatheter valve prosthesis into a crimped configuration for delivery within a vasculature, wherein the crimper applies pressurized fluid in a radial direction to at least one leaflet of the transcatheter valve prosthesis to displace the at least one leaflet radially inwards when the crimper is radially compressing the transcatheter valve prosthesis.

15. The method of claim 14, wherein the transcatheter valve prosthesis is partially compressed or fully compressed during the step of operating the crimper.

16. The method of claim 14, wherein the crimper includes a plurality of crimper elements that collectively define a crimper chamber of the crimper, and wherein at least one crimper element of the plurality of crimper elements includes an integral channel extending therethrough for applying the pressurized fluid to the at least one leaflet.

17. The method of claim 16, wherein the step of operating the crimper includes reducing a volume of the crimper chamber of the crimper by causing the plurality of crimper elements to move radially inwards.

18. The method of claim 16, wherein the integral channel extends from an inlet to an outlet, the inlet being formed at a first end of the at least one crimper element and the outlet being formed at a second end of the at least one crimper element, the second end opposing the first end.

19. The method of claim 16, wherein the at least one crimper element includes a first end and a second end, the second end opposing the first end, and wherein the integral channel extends from an inlet to an outlet, each of the inlet and the outlet being formed closer to the second end than the first end of the at least one crimper element.

20. The method of claim 16, wherein the transcatheter valve prosthesis includes exactly three leaflets and the crimper includes exactly three crimper elements that each include an integral channel extending therethrough for applying the pressurized fluid.

* * * * *